US011501363B2

(12) United States Patent
Garcia Giraldez et al.

(10) Patent No.: US 11,501,363 B2
(45) Date of Patent: Nov. 15, 2022

(54) 3D PLATFORM FOR AESTHETIC SIMULATION

(71) Applicant: Crisalix S.A., Lausanne (CH)

(72) Inventors: Jaime Garcia Giraldez, Troistorrents (CH); Fabian Wyss, International (AE)

(73) Assignee: Crisalix S.A., Lausanne (CH)

( * ) Notice: Subject to any disclaimer, the term of this patent is extended or adjusted under 35 U.S.C. 154(b) by 380 days.

(21) Appl. No.: 16/853,499

(22) Filed: Apr. 20, 2020

(65) Prior Publication Data

US 2020/0242686 A1   Jul. 30, 2020

Related U.S. Application Data

(63) Continuation of application No. 14/766,720, filed as application No. PCT/EP2014/052414 on Feb. 7, 2014, now abandoned.

(51) Int. Cl.
| | |
|---|---|
| *G06Q 30/06* | (2012.01) |
| *G16H 50/50* | (2018.01) |
| *A61B 34/10* | (2016.01) |
| *G06T 19/20* | (2011.01) |

(Continued)

(52) U.S. Cl.
CPC ......... *G06Q 30/0643* (2013.01); *A61B 34/10* (2016.02); *G06Q 30/0269* (2013.01); *G06Q 30/0277* (2013.01); *G06Q 30/0282* (2013.01); *G06Q 30/0613* (2013.01); *G06Q 50/01* (2013.01); *G06T 19/20* (2013.01); *G16H 50/50* (2018.01); *A61B 2034/104* (2016.02);

(Continued)

(58) Field of Classification Search
CPC ........... G06Q 30/0643; G06Q 30/0269; G06Q 30/0277; G06Q 30/0282; G06Q 30/0613; G06Q 50/01; A61B 34/10; G06T 19/20; G16H 50/50
See application file for complete search history.

(56) References Cited

U.S. PATENT DOCUMENTS

| | | | |
|---|---|---|---|
| 5,315,512 A | * | 5/1994 | Roth ................... G01S 15/8993 600/443 |
| 7,587,075 B1 | | 9/2009 | Stefan et al. |

(Continued)

FOREIGN PATENT DOCUMENTS

| | | |
|---|---|---|
| WO | 2013004572 A2 | 1/2013 |
| WO | 2013005447 A1 | 2/2015 |

OTHER PUBLICATIONS

De Hera Ciechomski, P. et al: "Development and Implementation of a Web-Enabled 3D Consultation Tool for Breast Augmentation Surgery Based on 3D-Image Reconstruction of 2D Pictures", Internet Citation, Feb. 3, 2012, ISSN: 1438-8871 http://www.jmir.org/2012/1/e21/ Site accessed: Jan. 27, 2020.

(Continued)

*Primary Examiner* — Seth A Silverman
(74) *Attorney, Agent, or Firm* — Whitmyer IP Group LLC

(57) ABSTRACT

The present teaching is related to the field of aesthetics. It concerns more particularly new methods for the generation of 3D anatomical outputs and 3D simulations of any aesthetic procedure, products obtained by such simulations, uses thereof and the creation of platforms or 3D virtual worlds of connected users and entities forming a virtual community using such methods and creating or ordering accessories and/or products.

20 Claims, 20 Drawing Sheets

(51) Int. Cl.
*G06Q 30/02* (2012.01)
*G06Q 50/00* (2012.01)

(52) U.S. Cl.
CPC ..... *A61B 2034/108* (2016.02); *G06T 2200/24* (2013.01); *G06T 2219/2021* (2013.01)

(56) References Cited

U.S. PATENT DOCUMENTS

| | | | | |
|---|---|---|---|---|
| 2007/0288198 | A1* | 12/2007 | Massen | A61B 5/0064 |
| | | | | 702/167 |
| 2008/0159608 | A1* | 7/2008 | Suetens | A61B 34/10 |
| | | | | 382/128 |
| 2010/0030578 | A1* | 2/2010 | Siddique | H04W 4/00 |
| | | | | 705/26.1 |
| 2010/0312143 | A1* | 12/2010 | Kim | A61B 5/1079 |
| | | | | 600/587 |
| 2011/0270044 | A1 | 11/2011 | Kimmel et al. | |
| 2012/0078831 | A1 | 3/2012 | Newcott | |
| 2012/0130490 | A1 | 5/2012 | Emi et al. | |

OTHER PUBLICATIONS

Extended European Search Report Application No. 19159298.9 Completed: Nov. 27, 2019; dated Dec. 4, 2019 15 Pages.
Robbins, Erica: "Previsualize yourself with Crisalix's 3D Surgery Simulator", Sublimma, published May 22, 2012, XP002727395, retrieved from the internet: http://www.jmir.org/2012/1/e21/.

* cited by examiner

Listing orders

[New Order]

| Created at | Status | Comments | Patient | Total implants | |
|---|---|---|---|---|---|
| January 28, 2014 20:25 | ✓ Confirmed<br>January 29, 2014<br>11:23 | Lo quiero ya | 20140127_1757 | 2 implants | Details |
| January 28, 2014 20:33 | [Pending...] | test | - | 3 implants | Details |
| January 28, 2014 20:41 | [Pending...] | test | - | 2 implants | Details |
| January 28, 2014 20:43 | [Pending...] | test | - | 3 implants | Details |
| January 28, 2014 20:44 | [Pending...] | test | - | 2 implants | Details |
| January 29, 2014 11:16 | ✓ Confirmed<br>January 29, 2014 | test | - | 3 implants | Details |

*FIG. 20*

3D PLATFORM FOR AESTHETIC SIMULATION

TECHNICAL FIELD

The present teaching is related to the field of aesthetics. It concerns more particularly new methods for the generation of 3D anatomical outputs and 3D simulations of any aesthetic procedure, products obtained by such simulations, uses thereof and the creation of platforms or 3D virtual words of connected users and entities forming a virtual community using such methods and creating or ordering accessories and/or products.

BACKGROUND

In the aesthetic field, professional-patient communication is vital as the diagnosis, treatment and outcome are dominated by the patient's subjective assessment of the visual results of the elective surgical procedure. Failure to meet the patient's expectations (for example augmentation volume or breast projection) can lead to the need for re-operations and ultimately into legal action. It is therefore essential that the patient be personally involved in the process of implant selection, supported by a realistic visual representation of their body, the pre-visualization of the final result. The success of the surgical outcome depends significantly on the choice of implant shape, size, projection and anatomical placement and these are key factors in the decision process.

To date, available computerized 3D anatomical visualization can be divided into the following categories:

Image morphing techniques: solutions working exclusively in two dimensions and projecting potential outcomes directly in the photos.

Templates and predefined software which allows the user to define a set of parameters, relate them to a pre-defined model and a pre-defined outcome.

Educational software: use of avatars in virtual reality learning environments.

Three-dimensional scans: allow an accurate 3D modeling of the patient's specific shape and texture by means of hardware.

The above mentioned techniques have their inherent limitations for application in the daily clinical work of a professional.

Therefore, there was a need in the development of new procedures allowing the professional to better pre-visualize the impact of a proposed surgical procedure together with the patient, preferably directly during the consultation. There was a need in the development of novel procedures allowing enhanced pre-visualization of results acting therefore as a guide for the preoperative planning and decision process.

SUMMARY

The present teaching relates to novel methods using digital photos or videos for reconstruction into a 3D representation available for interactive planning to the user. The simulation may be performed on dedicated servers and/or accessible via internet.

In a first aspect, the present teaching provides a method of generating at least one 3D anatomical output, 3D representation and/or 3D simulation of an animal body or human body and/or of at least one part of said body consisting of or comprising:

i) receiving as input at least one image, at least one video and/or anatomical information (FIG. 1, 10)

ii) generating at least one 3D anatomical output from said body and/or of at least one part of said body (FIG. 1, 20), and iii) visualizing said 3D anatomical output (FIG. 1, 30).

In a second aspect, the present teaching provides a product, object, accessory, medical device, implant, sizer or any creation obtained by any method according to the present teaching.

In a third aspect, the present teaching provides a community or 3D virtual world of users and/or entities (FIGS. 12, 100, 140 and 150), wherein said community or 3D virtual world is an online platform characterized in that at least one user and/or entity of said community or 3D virtual world use at least one method according to the present teaching.

In a fourth aspect, the present teaching provides various uses of any method of the present teaching, of a product, object, medical device, implant, sizer or any creation according to the second aspect of the present teaching, or of a community or 3D virtual world according to the third aspect of the present teaching.

BRIEF DESCRIPTION OF THE DRAWINGS

The accompanying drawings, which are incorporated herein and form a part of the specification illustrate preferred embodiments of the present teaching, and together with the description, serve to explain the principles of the present teaching.

FIG. 16 is a screenshot representing the step of adding the credit card information to proceed to payment for the 3D service.

FIG. 19 is a screenshot representing a popup with the order form appearing after clicking on the button "knife". On it, the user may specify the implants to order, the surgery date, the delivery address and leave comments among others.

FIG. 20 is a screenshot representing a list of orders sent by the doctor, showing the date of ordering, their status (pending, confirmed, cancelled), and all details related to products and delivery.

DETAILED DESCRIPTION

The following paragraphs provide definitions of the terms according to the present teaching and are intended to apply uniformly throughout the specification and claims unless an otherwise expressly set out definition provides a broader definition.

The expression "3D representation" means 3D modeling of the body or any parts of the body of a human being or animal.

The expression "3D simulation" means a modified 3D representation following some requirements in order to represent a desired outcome.

A 3D representation or 3D simulation is herein to be considered as a 3D anatomical output.

The expression "Aesthetic professional" means any plastic, reconstructive or aesthetic surgeon, dermatologist, professional working on aesthetic or beauty centers, or any other professional practicing in the aesthetic field.

The expression "Consumer" means any person interested in aesthetics or beauty, or any person being a potential user of the owner's herein described application or system.

The expression "Human Body" means the entire structure of a human organism, comprising or consisting of a head, neck, torso, two arms and two legs.

The expression "point-of-care" means all services provided to patients at the bedside.

Figure 1:
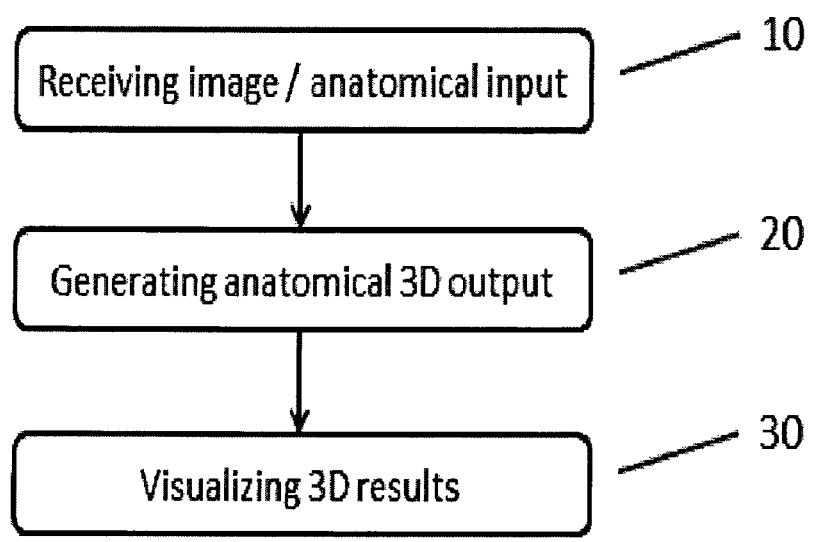
FIG. 1 represents the basic flow of generating a 3D representation.

As shown in FIG. 1, the methods and technology of the present teaching are based on the generation of 3D representations of the human or animal body, or parts of the human or animal body such as the face, upper body, lower body and back side (FIG. 1, 20), by using a certain number of images of it taken from different angles of view (FIG. 1, 10). Those images may be either standard digital photos or frames extracted from a video. Optionally, the system also works with a single image from one view. Optionally, the system may use 3D images taken from 3D photographic devices. Optionally, anatomical measures may be taken as input in order to scale the 3D representation to real size. Based on the anatomy of the body and information about the procedure the user wants to simulate, the system creates a 3D simulation of the final desired outcome. The 3D representation can be made of anybody using the system.

The whole process and methods of the present teaching may be provided as an online service, where the user must enter into his account by using identification such as login and password, or it can be an application running in a local machine such as a personal computer, tablet, smartphone, or any device being able to visualize 3D results to the user.

Accordingly, in a first aspect, the present teaching provides a method of generating at least one 3D anatomical output, 3D representation and/or 3D simulation of an animal body or human body and/or of at least one part of said body consisting of or comprising:

i) optionally accessing service (FIG. 7, 60),
ii) optionally starting process (FIG. 7, 70),
iii) receiving as input at least one image, at least one video and/or anatomical information (FIG. 1, 10)
iv) generating at least one 3D anatomical output from said body and/or of at least one part of said body (FIG. 1, 20),
v) optionally visualizing said 3D anatomical output (FIG. 1, 30),
vi) optionally linking users together, wherein said users are selected from consumers, professionals and companies (FIG. 7, 80),
vii) optionally creating at least one object, creation, product, accessory, implant and/or sizer (FIG. 5, 40),
viii) optionally online ordering of at least one product (FIG. 6, 50),
ix) optionally managing stock,
x) optionally data mining, and
xi) optionally producing statistics.

Figure 14:
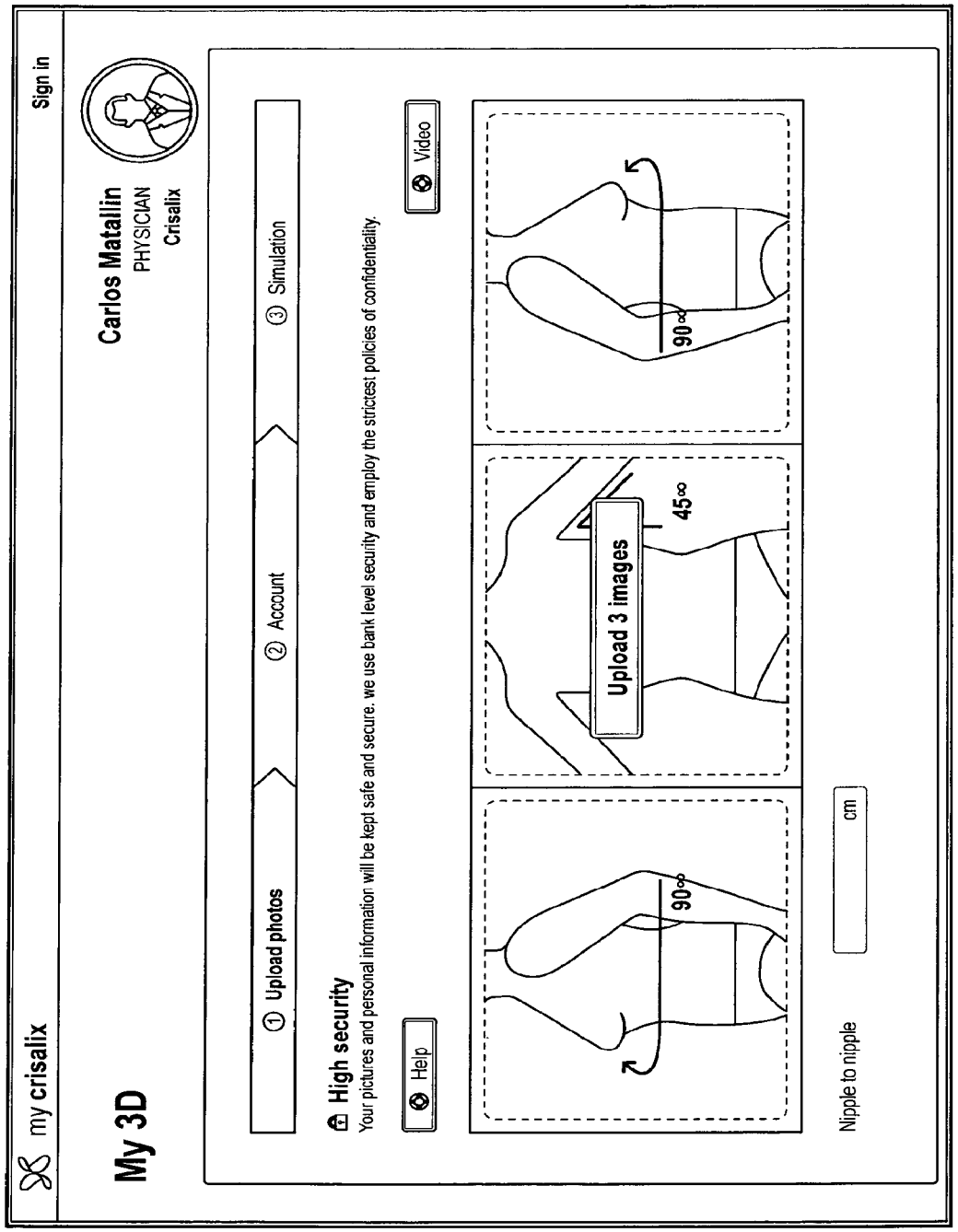
FIG. 14 is a screenshot representing the step dedicated to upload the 3 photos needed to create the 3D representation.

Advantageously, there is no need of special equipment or hardware dedicated to the acquisition of the images. Preferably, the images are the output of any imaging device (FIG. 2, 10.1), such as a standard digital camera, video camera, independent webcam or integrated in the computer, or smartphones and tablets equipped with camera. Optionally, the system may accept drawings as an input in exchange of images. In order to generate the 3D representation the system requires one or several images of the body preferably taken from different angles at a certain distance. The images may be directly standard digital photos or frames extracted from a video. Preferably, the video requires taking views from one or different angles (FIG. 2, 10.2; FIG. 14).

Optionally, if the user is using a mobile device, such as a smartphone or tablet, a mobile application is available so that the process of taking the photos or video and generating the 3D can be done directly with it. Optionally, this application guides the user through the process of the acquisition of photos/video by displaying guiding information directly on the screen, and/or by voice. Once the photos or video are acquired, the mobile application either sends them online to the server to start the 3D generation process or starts the 3D generation process directly in the mobile device.

Figure 2:
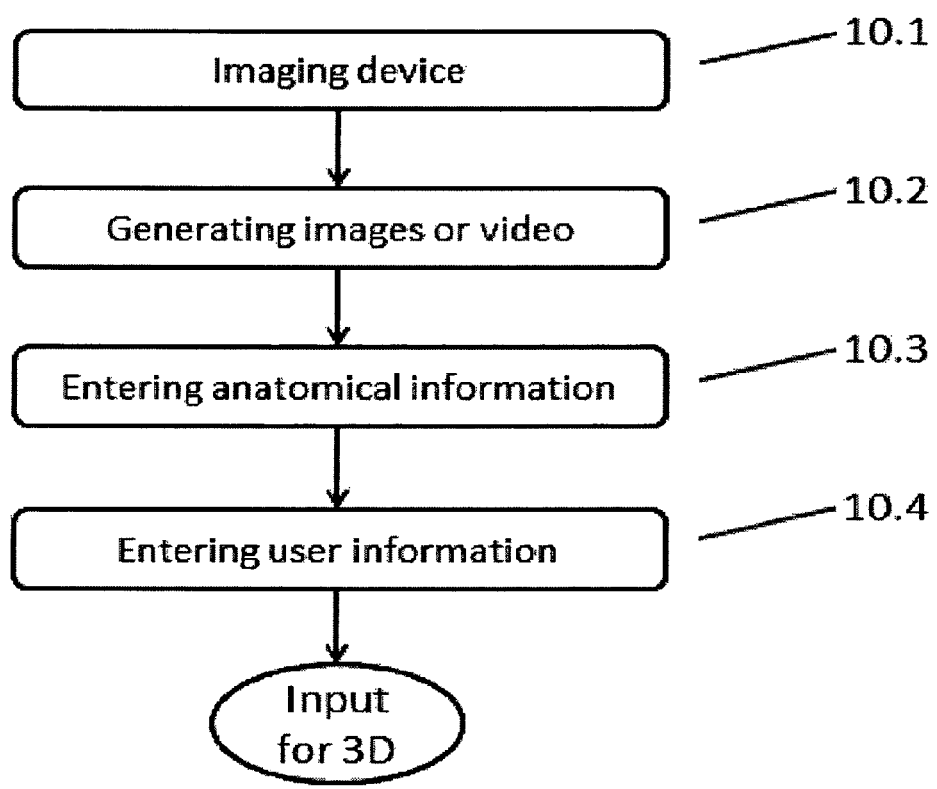
FIG. 2 represents the different information required as input for the 3D representation generation.

Optionally, the user may enter anatomical information about the body or part of the body to create the 3D representation (FIG. 2, 10.3). This information may be used for scaling purposes, so it must correspond to anatomical measures done on the body, such as distances between anatomical points, height, weight and/or age. Optionally, these measures may also be detected and calculated automatically by image analysis so the user does not need to insert them.

Optionally, the user may enter some information about the consumer creating the 3D. It may be contact information like email, phone number and address, or a medical profile to be kept for the records, and/or his interests (FIG. 2, 10.4).

All this information about the anatomy and the consumer to be modeled in 3D may be entered by the user directly to the system by any means.

Optionally, the imaging input information may be provided by medical devices such as MRI, CT or standard X-rays.

Accordingly, in a preferred embodiment, said accessing service of step i) of the first aspect of the present teaching is either located directly in a form of web banner in a website or any application belonging to a professional, in a website belonging to the owner of said service or system, in any other website with whom the owner of said service has an agreement with, in online social networks such as Facebook or Twitter, and/or accessible via any application, whether mobile phone, tablet, computer or laptop.

Accordingly, in a first preferred embodiment, said step iii) of the first aspect of the present teaching of receiving as input comprises or consists of:
  i) generating at least one image and/or at least one video with at least one imaging device (FIG. 2, 10.2),
  ii) optionally obtaining anatomical information by either automatic means and/or by manually entering said anatomical information (FIG. 2, 10.3), and
  iii) optionally obtaining user information by either manually entering said user information and/or by automatically retrieving said user information (FIG. 2, 10.4).

Figure 3:
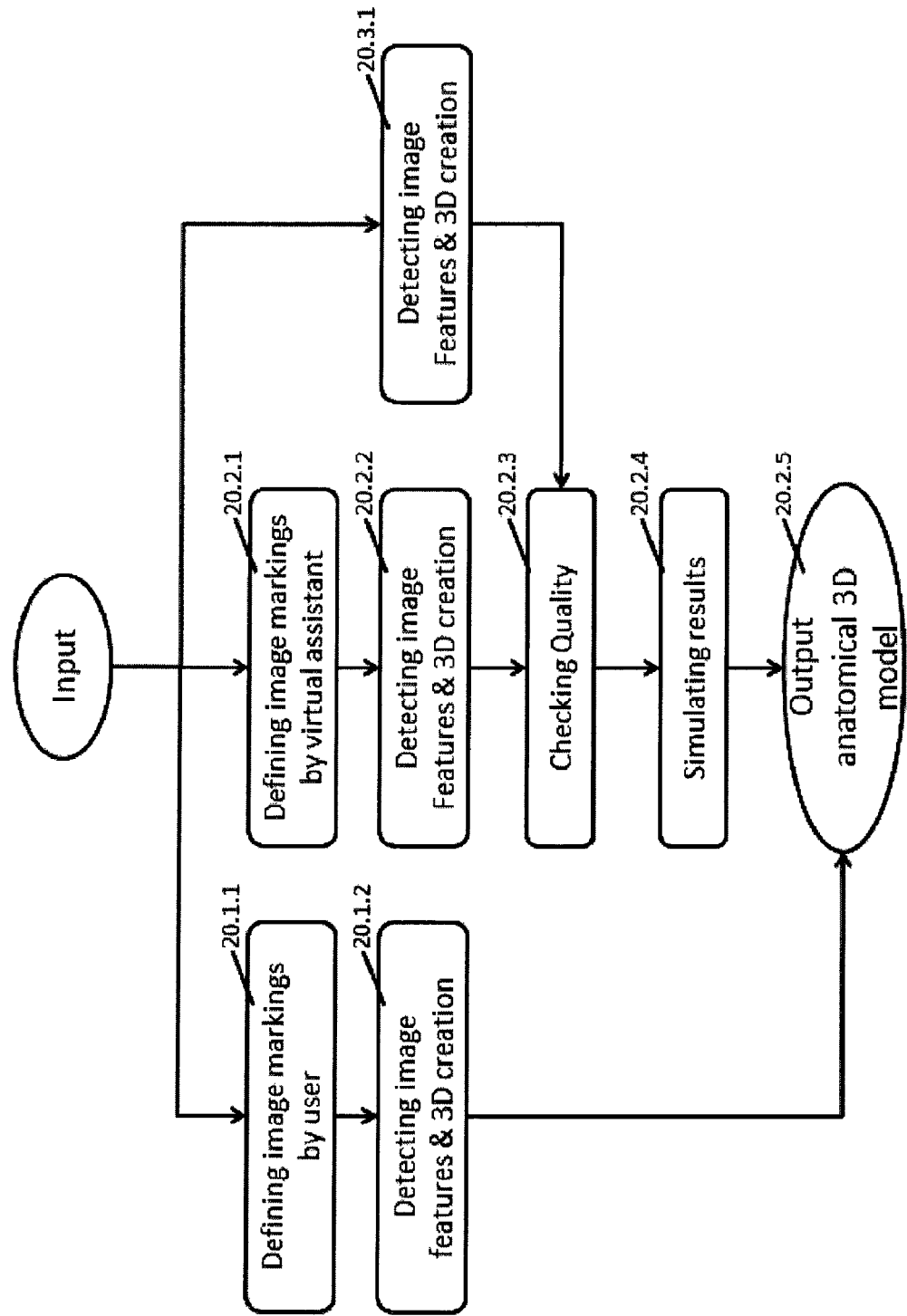
FIG. 3 represents how the 3D representation is generated.

The images and optionally the anatomical information are taken as input to generate the 3D representation of the consumer. Defining the image markings may be performed by the user, patient, professional, aesthetic professional, or a virtual assistant (VA). Preferably, the system automatically detects the image features and creates the 3D representation (FIG. 3, 20.3.1). The 3D representation created is the output passed on to the visualization step.

Optionally, the user may define several markings in the images as a previous step in order to help on the detection of features (FIG. 3, 20.1.1). This marking process may also be done by a support service provided by the software/application developer or owner, system owner, or outsourced to a third party company in order to simplify the process for the user, herein called virtual assistant or VA (FIG. 3, 20.2.1).

All the steps of any of the method herein described that may be performed by the user may be performed by a professional, aesthetic professional, or a virtual assistant (VA). All the steps of any of the method herein described that may be performed by a professional may be performed by a virtual assistant (VA). Such steps may be performed locally, point of care or in a remote location.

Optionally, there may be a quality control process to verify that the 3D representation created meet a minimum level of accuracy (FIG. 3, 20.2.3). In case such minimum level is not reached, the user or the VA may proceed to correct the 3D representation using a 3D shape and texture editor. In case the user decides the quality of the 3D representation received doesn't meet his quality requirements, the user may ask once again for example the VA to re-do the 3D representation, or the user or professional may retake images. Optionally, the VA may ask the user to take again the images or data to be sent.

Optionally, if the user requests one or several simulations of one or several procedures to the VA, the VA will prepare the simulations and will make them available for the user as output (FIG. 3, 20.2.4).

Accordingly, in a second preferred embodiment, said step iv) of the first aspect of the present teaching of generating at least one 3D anatomical output consists of or comprises:
  i) optionally defining image markings (FIG. 3, 20.2.1),
  ii) detecting the image features, preferably by automatic means (FIG. 3, 20.2.2),
  iii) creating at least one 3D anatomical output or 3D representation,
  iv) optionally checking the quality of said 3D anatomical output or 3D representation (FIG. 3, 20.2.3),
  v) optionally correcting said 3D anatomical output or 3D representation and/or regenerating said 3D anatomical output or 3D representation,
  vi) optionally generating at least one novel input according to any of the previous claims,
  vii) optionally selecting at least one 3D procedure or 3D simulation feature, and
  viii) optionally simulating at least one 3D anatomical output based on said 3D procedure or 3D simulation feature (FIG. 3, 20.2.4).

The output of the 3D generation process is the input for the visualization and simulation step. Once the 3D representation is created, the user may visualize it in the 3D interface of the application. In case one or several simulations of a procedure were requested, the user may also visualize them (FIG. 4, 30.1).

Optionally, the system may provide the user with different planning methods available in the market for implant surgery, for example breast surgery.

Figure 4:
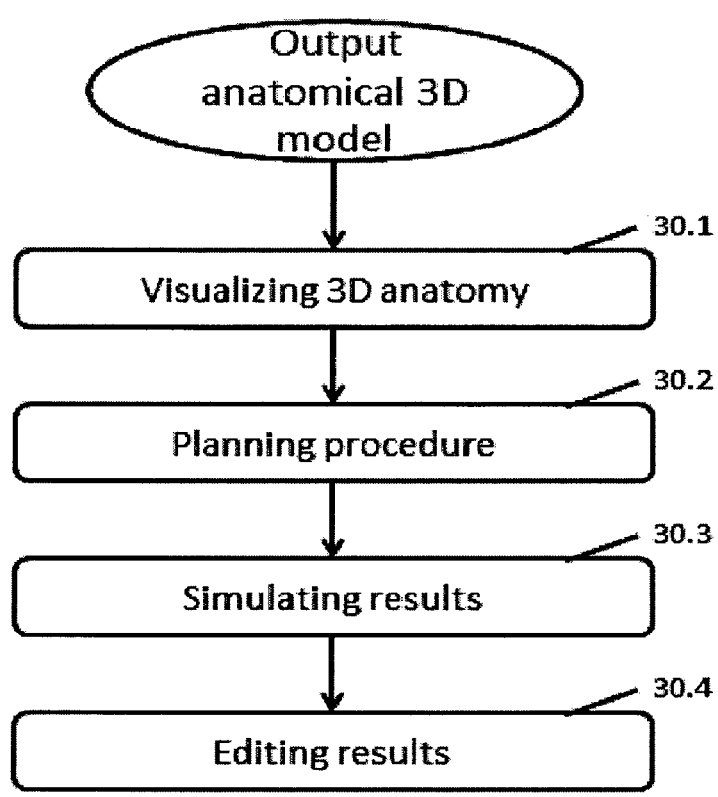
FIG. 4 represents how the 3D representation is given to the professional and different options available.

Optionally, in the case of an implant procedure, for example for a breast implant procedure, the user may use a planning system where he can analyze the anatomy and select the best implant to be used (FIG. 4, 30.2).

The system may include a simulation engine that may be used by the user to generate the outcome of any aesthetic or plastic procedure (FIG. 4, 30.3). Preferably, based on the information provided by the user, for instance the breast implant characteristics in case of doing a breast augmentation, the system may generate a 3D estimation of what could be the result in the anatomy of the consumer.

Optionally, the system may provide the user with a catalogue of implants, e.g. breast implants, that he may use to select the implants for the simulation. This catalogue may contain all the brands and types available in the market, and the user may find the best implants using as input any of the parameters that define an implant such as diameter, projection, volume, height, width, shape, reference, brand, profile type and/or material. It may contain implant information for both aesthetic and reconstructive procedures. The catalogue may be used statically or dynamically. Statically means showing the whole catalogue of implants and the user may navigate through the categories until finding the desired implant. Dynamically means providing the user with some search tools to input the parameters and the catalogue may display the closest implants fitting the defined search.

Optionally, for searching purposes the catalogue may recognize both keyboard and voice recognition input.

Optionally, the user may be able to store the favorite's implants of the user in order to optimize the search. The system may also learn about the user behavior so it automatically proposes implants or techniques that could fit based on previous cases.

Optionally, the catalogue may propose the user with a set of several recommendations of the most suitable implants for the consumer's anatomy, as well as the best position and/or surgical technique. Such recommendation may be based but not limited to the consumer's anatomy, consumer's desires, psychological and sociological aspects, statistical analysis of similar consumers and successful experiences, and/or aesthetic professional's decisions.

Optionally, the system may provide the user with a catalogue of different anatomies in order to simulate an outcome. These anatomies may be different types of noses for rhinoplasty, types of lips, types of eyes and eyebrows, types of chin and cheeks, types of haircuts, types of ears, and/or types of skin among others. Once selected, the system may transform the 3D anatomy of the consumer into the anatomy of the outcome selected.

Optionally, the system may provide the user with a 3D editor tool (FIG. 4, 30.4). The editor may provide the user with several tools that allow modifying the 3D anatomy of the consumer.

Optionally, in order to provide the simulation of a procedure on the 3D representation of the consumer, the system may simulate changes in the internal organs and tissues of its body. By using the information of the consumer, such as the images and measurements, the system may create not only the 3D representation of the surface, but may also predict the shape of internal components. For instance, aesthetic or plastic procedures such as breast augmentation, rhinoplasties or cranio-maxillo-facial surgeries among others, imply changes or additions in internal parts of the body. The system may simulate those changes and/or additions, both forwards and backwards. Forwards means simulating the changes and/or additions in the internal part and then the system simulates the result in the shape of the 3D representation accordingly. Backwards means simulating the desired 3D shape of the representation and then the system simulates the changes and/or additions to be done in the internal part of the body to obtain such result.

Optionally, the system may provide the user with a backwards simulation. In this process, the user first defines the final outcome, and then the system calculates what to do to reach such outcome. In the case of a breast augmentation it could be the best implant, surgical technique and/or position. In the case of a chin or cheek implants it may be also the best implants and/or positions.

Optionally, the system may provide the user with tools to compare results before and after simulation. Such tools may allow the user to visualize in the same screen the 3D representations before and after in a split view, and/or showing progressively the change from before to after into the same anatomy.

Optionally, the system may provide a printout option wherein the user may select the outcomes he wants to add into it, as well as the information to be contained. This printout may then be printed in paper, sent to an email recipient, and/or stored in the profile of the consumer into the system.

Optionally, the printout may be done in a form of video with the results that may then be sent by any electronic messaging system and/or copied in a physical storage unit.

Optionally, the printout may be done in a form of a 3D file that may then be printed with a 3D printer device.

Optionally, the visualization of the 3D outcomes may be done or shown in a computer or TV screen, in a mobile device such as smartphones, tablets or laptops, using a projector, or the system may generate a 3D output that may be used for visualization in special screen devices that support 3D images with or without 3D glasses, and/or generate an output for an holographic visualization system in order to create a more immersive 3D environment.

Optionally, by using image tracking algorithms, the system may retro-project the results of the 3D outcome directly to the images of the consumer, generating as such augmented reality visualization. This augmented reality effect may also be generated by modifying the real image of the consumer in real time in order to obtain the desired outcome, both using a static photo or in the video stream, and/or using a specific mirror-screen to project the virtual images over the consumer.

Accordingly, in a third preferred embodiment, said step v) of the first aspect of the present teaching of visualizing the 3D anatomical output consists of or comprises:

i) visualizing 3D anatomy, at least one 3D anatomical output, 3D representation and/or 3D simulation (FIG. 4, 30.1), ii) optionally planning at least one 3D simulation procedure or 3D implant simulation procedure (FIG. 4, 30.2), iii) optionally simulating 3D anatomical output based on (FIG. 4, 30.3):
  a) the information provided by the user,
  b) the automatic analysis of said 3D anatomy, said 3D representation or said 3D anatomical output of step i),
  c) the selection of at least one implant, object, accessory and/or product from a catalogue or database of implants, objects, accessories and/or products, and/or,
  d) the selection of at least one type of anatomy from a catalogue or database of different anatomies, wherein said type of anatomy is selected from a type of nose, type of lips, type of eyes or eyebrows, type of chin and cheeks, type of haircuts, type of ears, and/or type of skin, iv) optionally editing said 3D anatomical output (FIG. 4, 30.4), v) optionally, preferably automatically, a) determining modifications in the shape of internal components or parts of the body following at least one 3D procedure or 3D simulation feature and b) simulating a 3D anatomical output based on said modifications, vi) optionally, preferably automatically, a) simulating at least one 3D desired anatomical output following at least one 3D procedure or 3D simulation feature and b) determining, preferably automatically, the resulting customized object(s), accessory(ies), creations(s), products(s), implant(s), sizer(s), surgical technique(s), anatomical position(s), modification(s) in the shape of internal components or parts of the body based on said 3D desired anatomical output, vii) optionally visualizing and comparing 3D anatomical output before and after simulation, wherein said visualization consists of either a split view or an animation showing progressively the change in the anatomy, viii) optionally visualizing, holographic visualizing, retro-project visualizing, augmented reality visualizing, storing, printing, customized printing, sharing, and/or sending any 3D anatomical output in either 2D form or 3D form, either as a video or image, and/or either in a remote location, locally or point of care, ix) optionally producing or manufacturing said 3D anatomical output or said resulting customized object(s), product(s), accessory(ies), implant(s), sizer(s), surgical technique(s), anatomical position(s), and/or modification(s) in the shape of internal components or parts of the body based on said 3D desired anatomical output, either in a remote location, locally or point of care.

In one embodiment, the present teaching provides a method consisting of or comprising:

i) receiving input,
ii) generating 3D representation,
iii) visualizing 3D representation,
iv) selecting 3D procedure or 3D simulation feature,
v) generating 3D simulation from said 3D procedure or 3D simulation feature, and
vi) visualizing 3D simulation.

Optionally, the system may provide the user with a tool to load and save the outcomes for further visualization.

Optionally, the user may create an online access so the 3D results may be visualized remotely after the consultation and/or shared with others.

Optionally, if the user needs assistance on performing a simulation, he may click or use the virtual assistant option and request the type of procedure desired. The virtual assistant may then generate the outcome for the user.

Optionally, the planning methods may provide guidelines to select the optimal implant sizes based on anatomical measures in the anatomical region, e.g. breast area, before surgery, which are then translated into specific measures in terms of diameter, projection and/or volume of implants. Since the 3D representations created may be scaled to the consumer's real size, those anatomical measurements may be directly provided to any method of the present teaching.

Optionally, the user may store his planning methodology for further usage in other consumers.

Optionally, the system may provide the user with simulations without the need of giving the characteristics of the implants, for instance visualizing a range of different sizes, or simulating based on attractiveness and/or anatomical proportions criteria.

In a fourth preferred embodiment, the present teaching provides a method according to the third preferred embodiment, wherein said simulating of step iii) automatically selects optimal object, creation, accessory, product or implant characteristics and/or anatomical position outcome, and/or wherein said simulation is performed by visualizing a range of different sizes, and/or is based on the attractiveness and/or on anatomical proportions criteria.

These tools available from the 3D editor tool may be used to add and/or remove volume in a region selected in the anatomy in order to simulate fat injection and/or any other substance used for this purpose, to modify or smooth the shape of a region and/or to modify the skin texture. These tools may be available as free-hand tools and/or using pre-defined areas by the system.

Accordingly, in a fifth preferred embodiment, the present teaching provides a method according to the third preferred embodiment, wherein said step iv) of editing permit modifying the 3D anatomical output comprising:
  adding and/or removing volume in a region selected in the anatomy for fat injection simulation and/or any other substance used for this purpose, and/or
  modifying and/or smoothing the shape of a region or skin texture.

Optionally, the planning system allows the user to calculate the volume of the anatomical region, e.g. the breasts, before the procedure, to analyze potential asymmetries, to calculate the orientation of the anatomical region, e.g. the breasts, before and after the procedure, to make drawings over the surface of the 3D representation, to make both linear and/or geodesical measurements in the anatomy, to display a symmetry plane in the middle of the body and project one side to the other in order to visualize anatomical differences, to select a pair of implants or only one implant from a catalogue and project them into the 3D anatomy in order to select the position inside the body, to identify the final shape and size and the system automatically calculates the corresponding implants to obtain such result or final shape, to calculate the optimal position of the implant after surgery, e.g. the sub-mammary fold, and to make annotations in the 3D anatomy.

Optionally, the system itself may provide the user with the best implant characteristics and/or the optimal position in the anatomy based on the analysis of the 3D anatomical model generated.

Accordingly, in a sixth preferred embodiment, the 3D implant simulation procedure consists of or comprises:
  i) optionally analyzing the anatomy and selecting best or appropriate implant(s) to be used,
  ii) optionally calculating the volume of the anatomical region before the procedure,
  iii) optionally analyzing potential asymmetries,
  iv) optionally calculating the orientation of the selected anatomical region before and/or after the procedure,
  v) optionally making drawings over the surface of the 3D representation,
  vi) optionally making linear and/or geodesical measurements in the anatomy,
  vii) optionally displaying a symmetry plane in the middle of the body and projecting one side to the other in order to visualize anatomical differences,
  viii) selecting at least one implant from a catalogue and projecting said implant(s) into the 3D anatomy in order to select the position inside the body and to create the final 3D anatomical output or 3D simulation,
  ix) optionally identifying/selecting the final shape and/or size enabling automatic calculation of the corresponding implant(s) of said selected final shape and/or size,
  x) optionally calculating the optimal position of the implant after surgery, and
  xi) optionally making annotations in the 3D anatomy.

Optionally, the system may provide a planning system for other parts of the body, such as facial implants, gluteus implants, muscle implants or any other implant used in the plastic, reconstructive or aesthetic field.

The fifth preferred embodiment relates to a 3D implant simulation procedure. The present teaching also encompasses a procedure not necessarily requiring the use of implants.

Accordingly, in a seventh preferred embodiment, the 3D simulation procedure consists of or comprises:
  i) optionally calculating the volume of the anatomical region before the procedure,
  ii) optionally analyzing potential asymmetries,
  iii) optionally making drawings over the surface of the 3D representation,
  iv) optionally making linear and/or geodesical measurements in the anatomy,
  v) optionally displaying a symmetry plane in the middle of the body and projecting one side to the other in order to visualize anatomical differences,
  vi) selecting at least one tool allowing modification of the shape and/or texture of said anatomical region in order to create the final 3D anatomical output or 3D simulation,
  vii) optionally selecting pre-defined shapes of the anatomical region under treatment in order to automatically try different templates, and
  viii) optionally making annotations in the 3D anatomy.

Optionally, the system may provide the user with a set of tools to simulate Botox®, dermal fillers, fat injection or any other dermatological procedure. The user may either work at a level of texture visualization, volume and/or surface.

Optionally, the system may provide the user with a set of tools to simulate real life movements of the body involving gravity effects, like jumping, running and/or different positions of the body anatomy. Also movements related to breathing and its impact in the breast shape, facial expressions, and changes in muscular shapes, growth, impact of the weight gain/loss, and/or impact of the aging process.

Optionally, the system may provide the user with a set of tools to simulate aging changes in the human body or parts of it, and/or the effects of the age in the procedure selected.

Accordingly, in an eight preferred embodiment, the present teaching provides a method according to any aspects or embodiments of the present teaching, further comprising simulating:
  i) an additional procedure selected from a Botox® procedure, dermal fillers procedure, fat injection procedure and/or any other dermatological procedure,
  ii) real life movements of the body involving gravity effects like jumping, running and/or different positions of the body anatomy, movements related to breathing and its impact in the breast shape, facial expressions, changes in muscular shapes, growth, impact of the weight gain/loss, and/or impact of the aging process, and/or
  iii) aging changes in the human or animal body or any part of it, any aging effect in the procedure selected.

In said additional procedure, the user may either work at a level of texture visualization, volume and/or surface.

An implant sizer is a breast implant made just for testing purposes, not to be implantable. Aesthetic professionals normally have some of them with different sizes, provided by the implant manufacturers, so when a consumer comes for a consultation, they try together what could be the best size by putting them inside their bra and looking at the mirror with an adjusted t-shirt. The number of implant sizers provided by the manufacturers is limited in number of shapes and volumes.

Concerning breast implants, manufacturers provide catalogues of implants with a range of sizes and shapes in order to better fit into the population. However, every consumer's anatomy is different so sometimes the implants available are not optimal for their anatomy.

Figure 5:
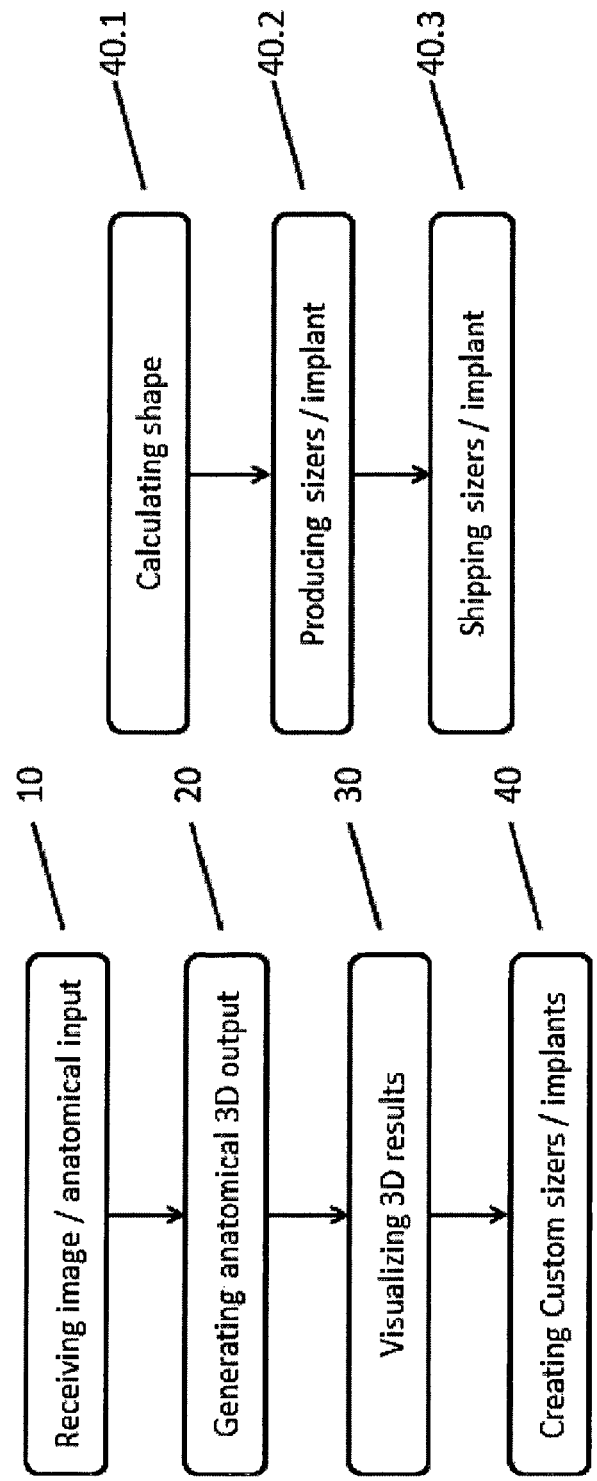
FIG. 5 represents the different steps involved in the generation of the custom sizer/implant and its production.

After simulating the breast augmentation procedure in 3D (FIG. 5, 30), the user has the option to order either a customized sizer and/or customized implant (FIG. 5, 40). Once ordered, the system may generate the shape of any or both devices.

After calculating the shape of the device, the production process is different for sizers and implants (FIG. 5, 40.2). The production of custom sizers may be done by an external manufacturer on demand, internally by using standard 3D printers, and/or directly by the users if they have a 3D printer available.

After production, the custom sizers or implants may be shipped to the user by any standard shipping service (FIG. 5, 40.3). Optionally, the user may set the priority of its production at the moment of ordering. The address of the receiver may be the user himself or the consumer in case of a sizer.

Optionally, if the user has a 3D printer available, there is no shipping process. The user may create the custom sizer and immediately print it and have it ready to use. Alternatively the user may send it directly to the consumer if he is doing everything remotely.

Optionally, the system may provide the user with a 3D printer specially designed to produce custom implants, creations, objects and/or products. In case of implants and medical related products and objects, such device may use bio-compatible materials in order to produce in 3D the shape of the desired implant, objects and/or products, being directly ready to be used in or on the human body.

Accordingly, in a ninth preferred embodiment, said step vii) according to the first aspect of the present teaching of creating at least one object, creation, product, custom sizer and/or implant consists of or comprises:
  i) determining the shape of said object, creation, product, accessory, implant or sizer (FIG. 5, 40.1),
  ii) producing said object, creation, product, accessory, implant or sizer (FIG. 5, 40.2), and
  iii) optionally shipping said object, creation, product, accessory, implant or sizer (FIG. 5, 40.3).

The system may calculate the shape of any or both devices according to:
  1. Custom sizer: the system calculates the shape to be added to the existing breasts, and this shape may then be sent for production.
  2. Custom implant: the system lets the user define the shape of the implant used for simulation and visualize the results in 3D. Once the user selects the final shape of the implant, this shape may then be sent for production.

Accordingly, in a tenth preferred embodiment of the present teaching, said step i) of the ninth preferred embodiment of the present teaching of determining the shape of said sizer is performed by automatically calculating the shape to be added to the existing breasts, and wherein said step i) of determining the shape of said implant is performed by manually defining the shape of the implant used for simulation and 3D anatomical output until final shape selection.

Figure 6:
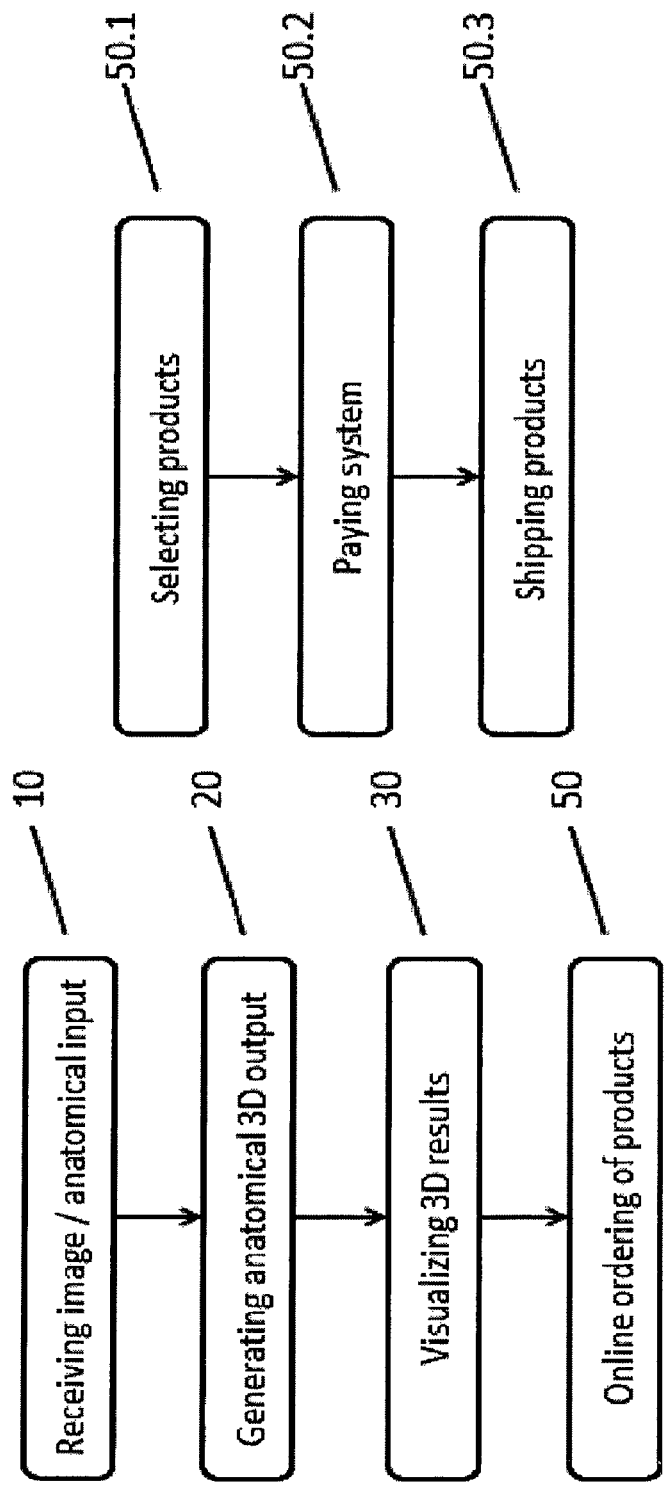
FIG. 6 represents how the process of selecting and ordering products is integrated in the system.

Being an online application with direct access to the user, the system may act as a marketplace or lead generator for medical devices such as breast implants, Botox®, dermal fillers, and/or any other type of medical device or aesthetic procedure. Once the user is at the visualization and simulation step (FIG. 6, 30), the user may simulate using the products available in the catalogue included in the product. Optionally, the system may show products available in the market related to the procedure the user is simulating. For instance, if the user is simulating a rhinoplasty, the system may show related products such as sutures or plates. At any step in any method of the present teaching, the user may select the products he would like to use or order, and add them into a shopping cart (FIG. 6, 50.1). At any moment, the user may go to the list of products selected and proceed to checkout.

Optionally, the system has a stock management tool for all products used by the user. The user may maintain this tool updated manually or letting the system to automatically update it any time the user does a simulation using specific products. If the procedure is confirmed with the products selected, the stock manager may take out the units used.

Optionally, the stock management tool may warn the user if he is running out of enough units of specific products. The user may proceed to order more products both from the simulator itself as specified above and/or from inside the stock management tool.

Optionally, the stock management tool may generate statistics in usage, projections for short and long term usage so the user may optimize the ordering of products, and/or analyze possible trends in usage.

Once the user proceeds to checkout, the system may check availability with the manufacturer(s) of the products. Optionally, several products available may be already manufactured by the system itself.

A product may herein be defined, but not limited to, as a creation, object, accessory, 3D procedure, 3D simulation feature, 3D feature, medical device, implant and/or sizer.

Once all the information is completed, the user may proceed to pay by any online payment method, bank transfer or equivalent (FIG. 6, 50.2). Then the order may be sent to the respective distributor and the products sent back to the user (FIG. 6, 50.3). Optionally, the user may set a priority on the shipping of the products bought.

Optionally, the system may give the option to pay after reception or use a credit line. Any kind of payment method could be used such as credit card, wire transfer, PayPal and/or cash.

Optionally, the user may have a credit inside the system which may be used for buying products and recharged any time needed.

Accordingly, in an eleventh preferred embodiment, said step viii) of the first aspect of the present teaching of online ordering of products consists of or comprises:
  i) selecting at least one product (FIG. 6, 50.1),
  ii) paying through a paying system (FIG. 6, 50.2), and
  iii) shipping said product(s) (FIG. 6, 50.3).

In a twelfth preferred embodiment, said product of the eleventh embodiment of the present teaching is selected either from a catalogue of products available for simulation and/or from products available in the marketplace related to the user's simulation, and/or wherein said product is selected from clothes, glasses, medical device, implant, breast implant, Botox®, dermal filler, sutures, plates or any other product, object or accessory that may be integrated in a 3D simulation procedure.

Accordingly, in one embodiment of the present teaching, said selected products are added to a shopping cart.

The process of creating the 3D representation and simulating a procedure may be done by an aesthetic professional or it may also be started directly by the consumer itself without the need of a professional. The system may provide services that consumers may use to provide their data and obtain such 3D simulations. Such consumer access (FIG. 7, 60) may be located directly in a form of a web banner (example in FIG. 8) in the website or any other application used by the aesthetic professional, in the system's website or in any other website with whom the system's owner has an agreement with, in online social networks such as Facebook or Twitter, and/or being part of a mobile application.

Figure 7:
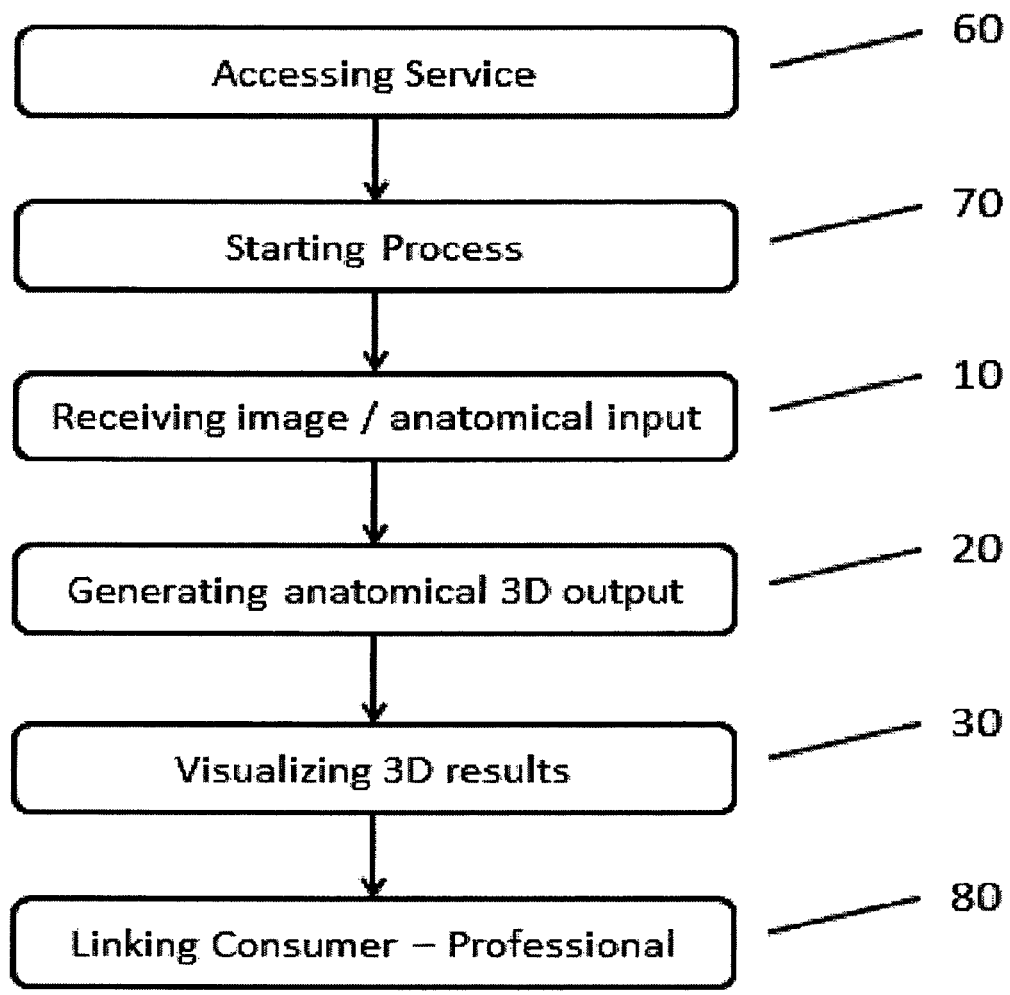
FIG. 7 represents the basic flow of the direct-to-consumer application.
Figure 8:
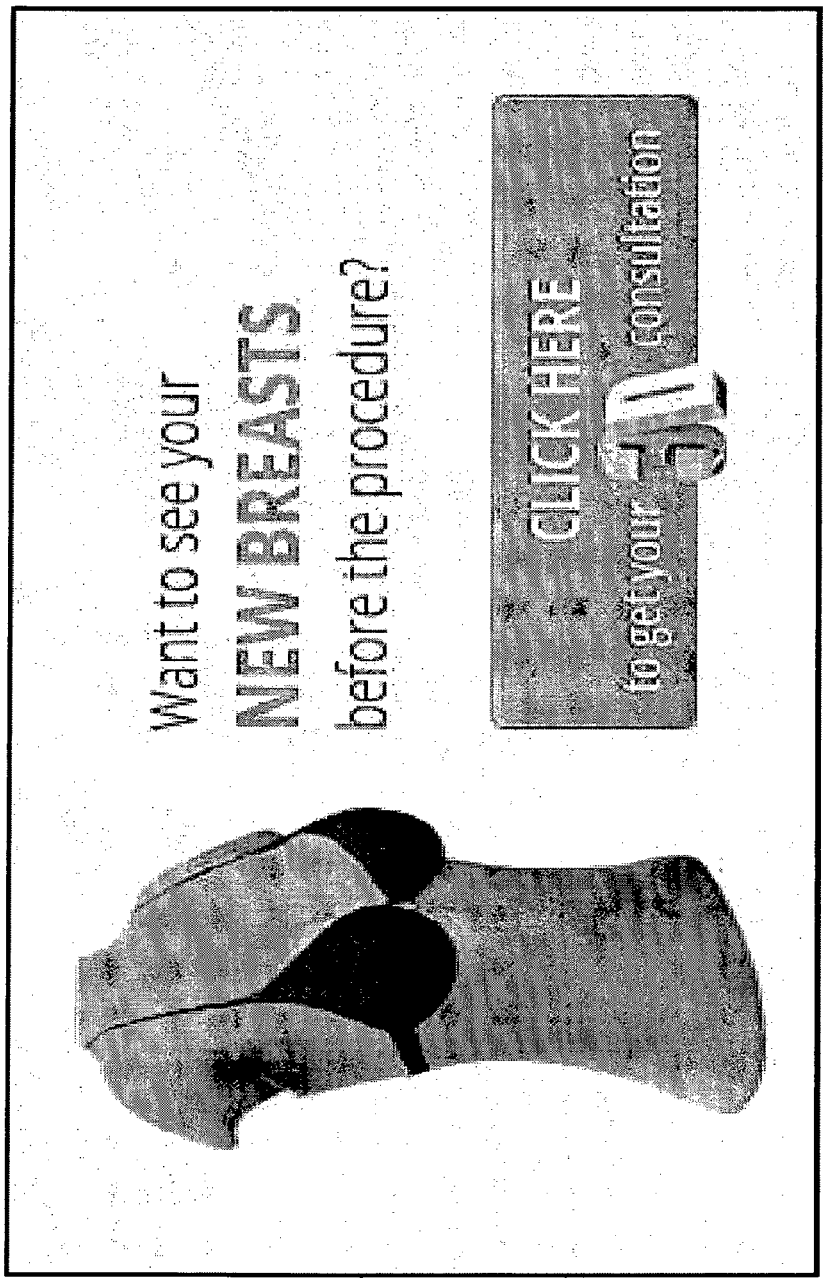
FIG. 8 represents an example of web-banner.

Accordingly, in a thirteen preferred embodiment, the present teaching provides (FIG. 7) a method of generating at least one 3D anatomical output, 3D representation and/or 3D simulation of an animal body or human body and/or of at least one part of said body according to the first aspect of the present teaching consisting of or comprising:
  i) optionally accessing service (FIG. 7, 60),
  ii) optionally starting process (FIG. 7, 70),
  iii) receiving as input at least one image, at least one video and/or anatomical information (FIG. 7, 10),
  iv) generating at least one 3D anatomical output from said body and/or of at least one part of said body (FIG. 7, 20),
  v) optionally visualizing said 3D anatomical output (FIG. 7, 30), and
  vi) optionally linking users together, wherein said users are selected from consumers, professionals and companies (FIG. 7, 80).

Preferably, the consumer is linked to the professional.

There are preferably two main services provided. The first one involves a professional in the process of generating the 3D representation and simulation of the consumer, and the second one may be directly done without the professional.

Figure 9:
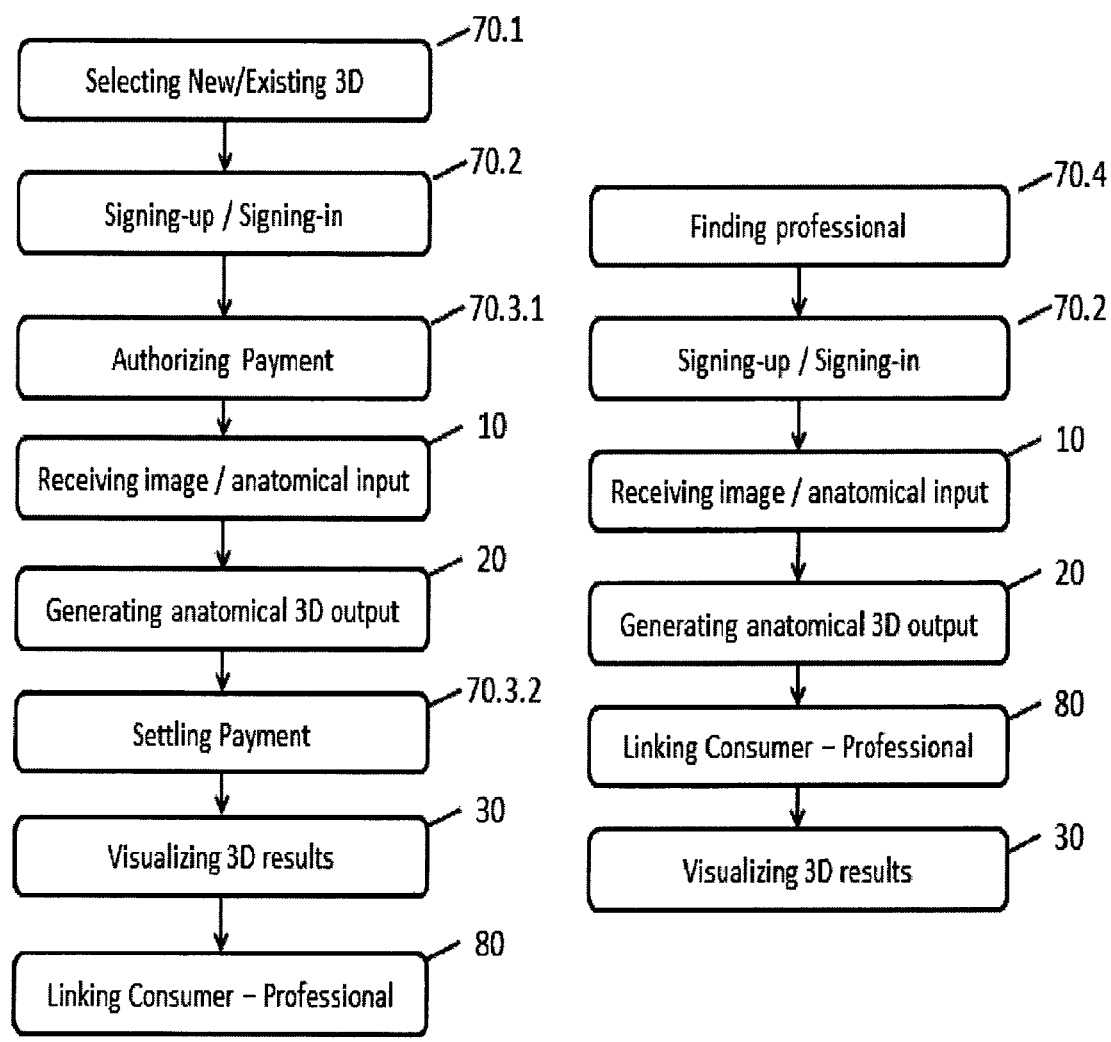
FIG. 9 represents the two different modalities of the direct-to-consumer approach. Left: consumer solution involving the consumer and the system. Right: consumer solution involving consumer, professional and the system.

The direct service for consumers gives the choice to create a new 3D representation and/or to visualize an existing one (FIG. 9, 70.1). Selecting an existing one visualizes the 3D representation and optionally simulations received (FIG. 9, 30). If the consumer is a new consumer of the service, he may be prompted to a sign-up process in order to create a new account. In the case of an existing consumer, he may sign-in into the system (FIG. 9, 70.2). Optionally, the system may store the account information so next time it automatically logs in the user. Before proceeding to the process of generating the 3D representation, the consumer may enter his payment information (FIG. 9, 70.3.1) with credit card, PayPal, mobile and/or any other electronic payment system available. Once the 3D representation is properly created and validated, the system may charge the consumer with the corresponding price related to the procedure selected (FIG. 9, 70.3.2). Optionally, different discounts may be applied to the price based on referrals, coupons and/or by sharing activity with other. After entering the payment information, the consumer may start with the process of taking and sending the images (FIG. 9, 10). The consumer may also enter its preferences in terms of simulation to be done. Once the 3D representation and simulations are available, the consumer may receive these results in form of images, video and/or directly in 3D visualization (FIG. 9, 30). After visualizing the results, the consumer may contact and optionally send the results to an aesthetic professional by using the professional finder tool available in the system or system's owner affiliates, to several at the same time, and/or send a message to any other professional not listed in this tool (FIG. 9, 80).

Figure 13:
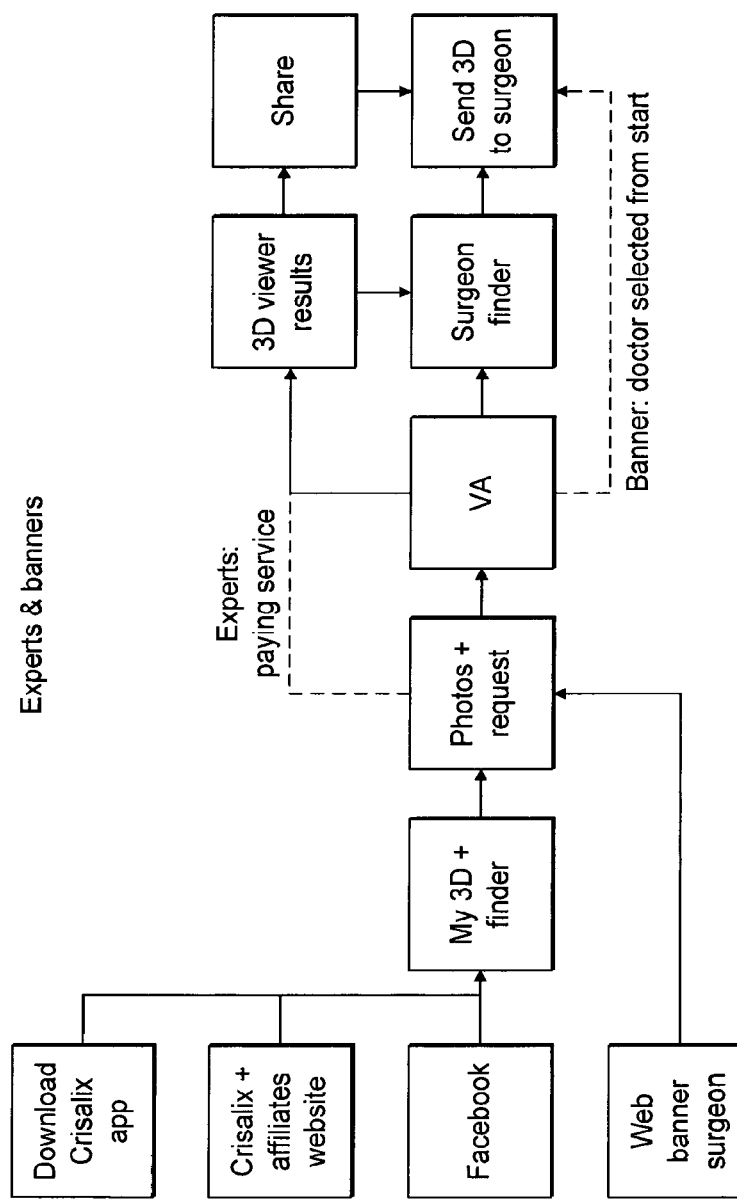
FIG. 13 illustrates the main services provided involving a professional in the process of generating the 3D representation and simulation of the consumer or directly done without the professional. Different options before the input including the web banner are represented, as well as the possible involvement of a virtual assistant in the procedure.

FIG. 13 illustrates as well the main services provided involving a professional in the process of generating the 3D representation and simulation of the consumer or directly done without the professional. Different options before the input including the web banner are represented, as well as the possible involvement of a virtual assistant in the procedure.

Accordingly, in a fourteen preferred embodiment, the present teaching provides a method of generating at least one 3D anatomical output, 3D representation and/or 3D simulation of an animal body or human body and/or of at least one part of said body according to the first aspect of the present teaching consisting of or comprising:
  i) selecting new or existing 3D representation or 3D anatomical output (FIG. 9, 70.1),
  ii) signing-up or signing-in (FIG. 9, 70.2),
  iii) optionally entering payment information (FIG. 9, 70.3),
  iv) receiving as input at least one image, at least one video and/or anatomical information (FIG. 9, 10),
  v) generating at least one 3D anatomical output from said body and/or of at least one part of said body (FIG. 9, 20),
  vi) optionally settling payment related to at least one selected 3D procedure or 3D simulation feature (FIG. 9, 70.3.2),
  vii) visualizing said 3D anatomical output first by user (FIG. 9, 30),
  viii) optionally linking consumer to professional (FIG. 9, 80),
  ix) optionally creating at least one custom product, object, creation, sizer or implant (FIG. 5, 40), and
  x) optionally online ordering of products (FIG. 6, 50).

The service involving professionals and consumers works as a service proposed by the professional itself through the system's technology. If the consumer enters into this service from a specific aesthetic professional selected, the 3D representation generated is sent directly to the professional's account as a new consumer available with all the information, selections and desires of the consumer. If the consumer enters through the system's owner website, its 3D representation does not have a receiver assigned yet. Such receiver may be found through the system's professional finder service or by any other service giving access to the system's professional users (FIG. 9, 70.4). The process of signing-up/in and sending the images and information, and the generation of the 3D representation is the same as for the direct solution. After receiving the 3D anatomical model and the information from the consumer, the aesthetic professional have several options available:

contact the consumer using the information received in order to propose a personal consultation with the goal of showing the consumer the 3D result(s) and simulation(s), prepare at least one simulation of the desired procedure(s), optionally print the results and send them to the consumer by any electronic messaging system having the advantage to convince the consumer to perform the procedure with this professional, do a web or phone conference with the consumer in order to show the consumer the result(s) remotely, and/or send back an access to the consumer to a second portal (FIG. 7, 70), where the consumer may log in and see the result(s) directly in 3D.

Accordingly, in a fifteen preferred embodiment, the present teaching provides a method of generating at least one 3D anatomical output, 3D representation and/or 3D simulation of an animal body or human body and/or of at least one part of said body according to the first aspect of the present teaching consisting of or comprising:

i) finding professional (FIG. 9, 70.4),
ii) signing-up or signing-in (FIG. 9, 70.2),
iii) receiving as input at least one image, at least one video and/or anatomical information (FIG. 9, 10),
iv) generating at least one 3D anatomical output from said body and/or of at least one part of said body (FIG. 9, 20),
v) linking consumer to professional (FIG. 9, 80),
vi) optionally visualizing said 3D anatomical output first by professional (FIG. 9, 30)
vii) optionally creating at least one custom product, object, creation, sizer or implant (FIG. 5, 40), and
viii) optionally online ordering of products (FIG. 6, 50).

Optionally, in both solutions, the consumer may send his 3D representation together with a request to all or a group of aesthetic professionals based on but not limited to different selection parameters such as location, ratings and/or reviews from other consumers, and/or procedures practiced. The aesthetic professionals receiving the request may answer by proposing an offer to the consumer so the consumer may select the best or more attractive offer.

In a second aspect, the present teaching provides a product, object, accessory, medical device, implant, sizer or any creation obtained by any method according to the present teaching.

By its unique solution, all users of the system are generating data related to their actions or inactions. Such data allows tracking consumer or professional behavior on an individual or group basis (FIG. 10, 90; FIG. 11, 90). Combination of those data allows generating statistics of any kind that are unique to the system's model.

The methods of the present teaching and/or the data mining, may be processed in a sequential or parallel manner, or both. For example, the system may generate 3D anatomical outputs, 3D representations and/or 3D simulations in a sequential or parallel manner, or by combining sequential and parallel. A user may select various 3D simulations and the system process the information in parallel, sequentially or both. Any treatment of the information may therefore be processed in a sequential or parallel manner, or both. Advantageously, parallel treatment may provide better efficiency. For example, if multiple users select at the same time 3D simulations, the system is able to treat the information either sequentially, in parallel or both. If the treatment is parallel, all 3D simulations may be visualized at the same time by all users and/or 3D simulations will be available in real time.

Figure 10:
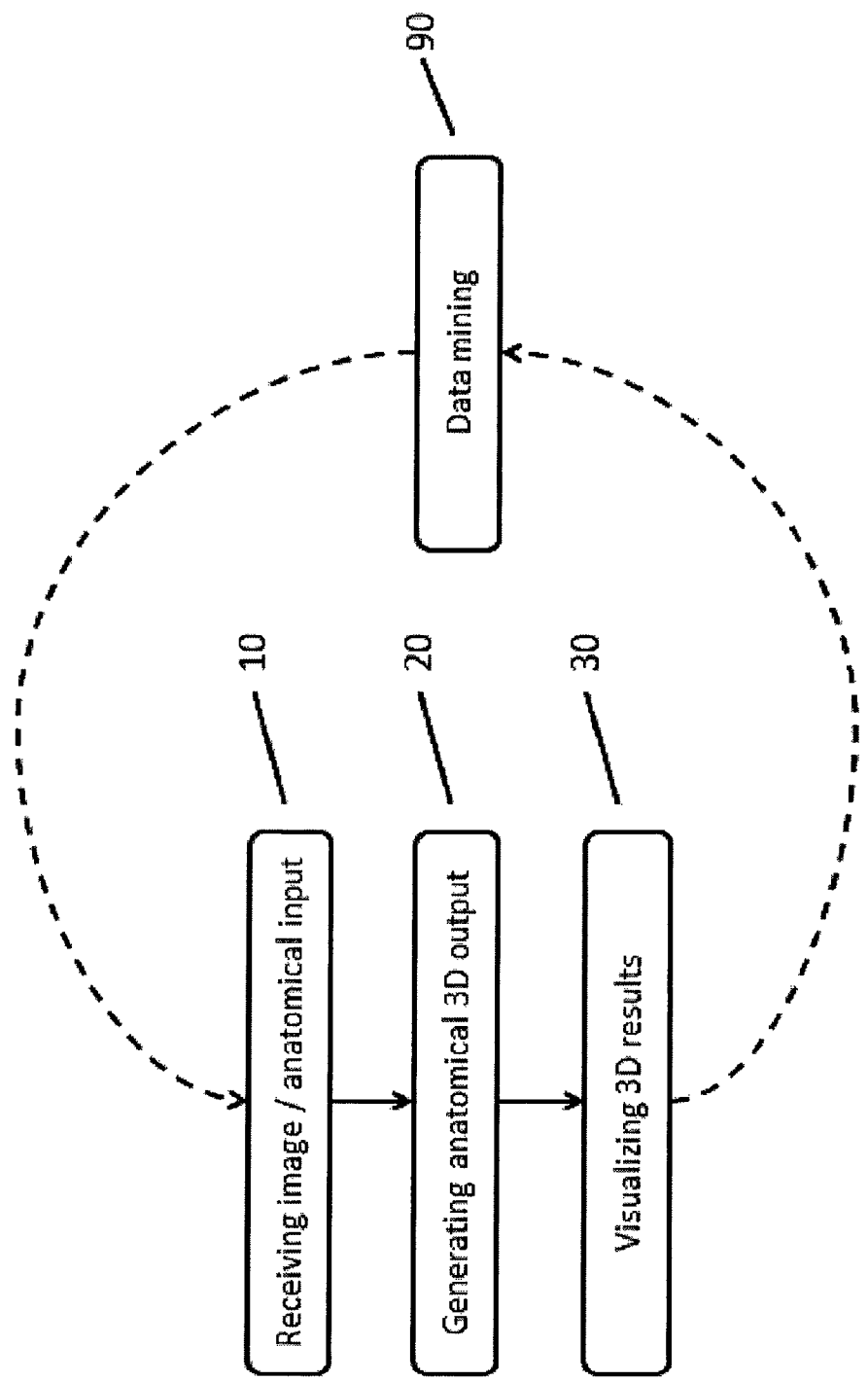
FIG. 10 represents the process of data mining and analysis of data in a sequential or serial manner.
Figure 11:
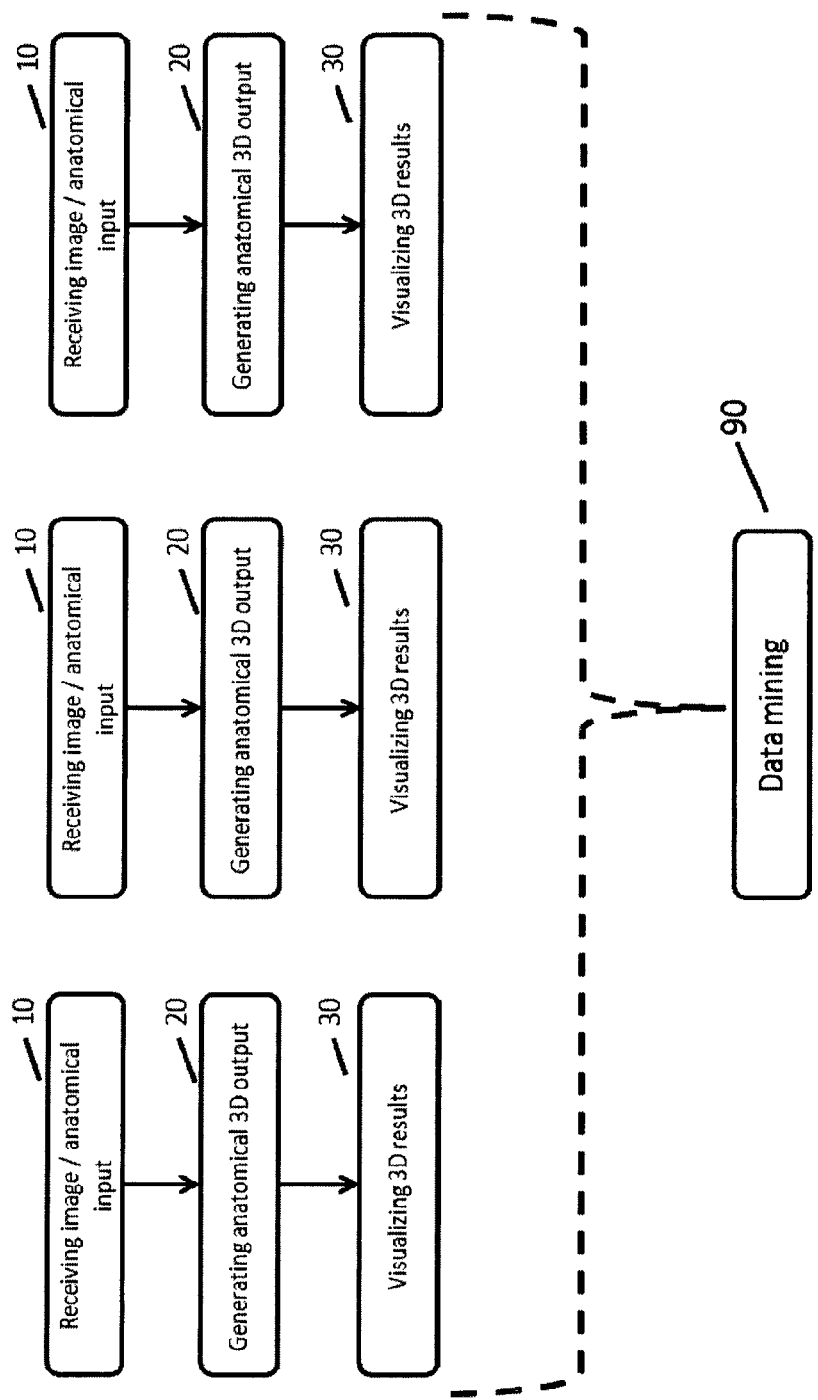
FIG. 11 represents the process of data mining and analysis of data in a simultaneous or parallel manner.

A sequential treatment of the information or data is shown in FIG. 10, whereas a parallel treatment of the information or data is shown in FIG. 11.

With a technology that allows any consumer to create a 3D representation or 3D simulation of its body or part of it, the system creates an online platform in a form of a community of users and entities, preferably with the focus on the aesthetic and beauty fields. The platform represents a virtual world where every user may have one or several 3D representations or 3D simulations associated and interact with other users. Aesthetic professionals and/or aesthetic or beauty companies or institutions may also be part of this community, with the abilities to also generate 3D representations or 3D simulations of their bodies, products and/or services, and interact with the community (FIG. 12).

The Platform is available either online and/or as a stand-alone application and may include users or entities generating at least one 3D anatomical output, 3D representation and/or 3D simulation, optionally linking consumer to professional, users or entities together, creating accessories and/or online ordering of products related to the procedure, and the ability to become a virtual community of users.

There are at least three different types of accounts: consumers, aesthetic professionals and aesthetic companies. Optionally there can be associations or groups.

Figure 12:
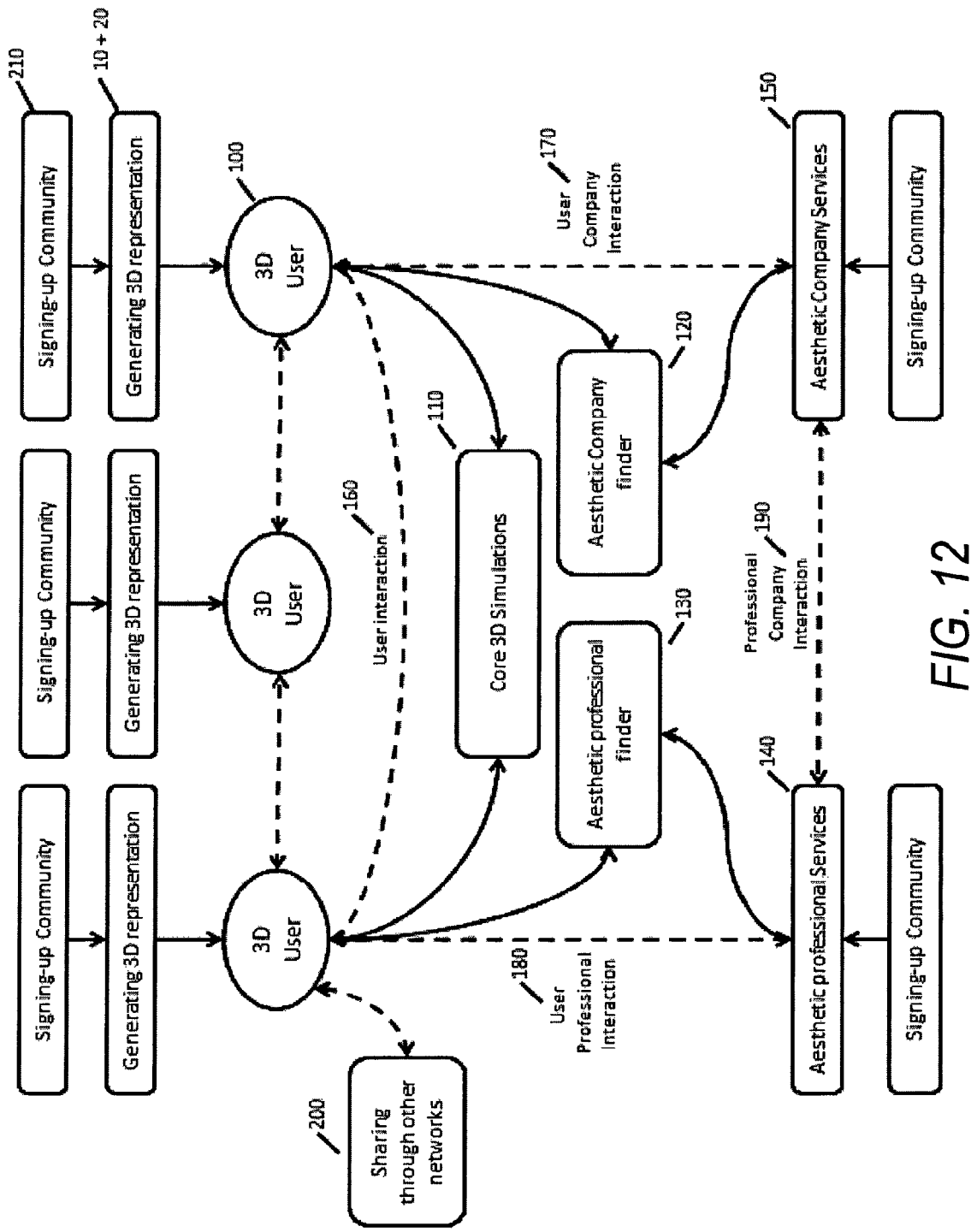
FIG. 12 represents the concept of the system's community and all interactions and tools available.

As a basic option a consumer may create his own 3D representations (FIG. 12, 10+20) and become a 3D user of the community (FIG. 12, 100). Optionally, he may simulate using the different simulation options available (FIG. 12, 110), interact with other users inside the community (FIG. 12, 160), use a search tool to find an aesthetic professional (FIG. 12, 130), use a search tool to find an aesthetic company providing services in the community (FIG. 12, 120), interact with aesthetic professionals (FIG. 12, 180) and aesthetic companies (FIG. 12, 170), and/or share the experience inside the community with other contacts through other social networks or communities (FIG. 12, 200).

As a community, a consumer may decide whether to stay private without any interaction with others or to be open to other users. Users may be able to interact between them at different levels of privacy in order to share information.

Aesthetic professionals may create an account and be part of the community. They can propose their services to all the users (FIG. 12, 140), be listed in the finder tool, be found by users and aesthetic companies and/or actively participate in the activities inside the community.

Aesthetic companies may create an account and be part of the community. They may propose their services to all the users and/or professionals (FIG. 12, 150), be listed in the finder tool, be found by users and aesthetic professionals and/or actively participate in the activities inside the community.

At least the following different types of users may interact between them, for instance:

Interaction between users (FIG. 12, 160):
a. make friendship requests, b. share 3D results with other users or groups of users,
c. comment in their own 3D results or others' results,
d. participate in public and/or private conversations,
e. put ratings in their own 3D results or others' results,
f. vote for best 3D results,
g. propose 3D visualizations of their friends to show them how they consider them the most attractive,
h. create videos with their own 3D results and share them with others,
i. participate in competitions between users, and/or
j. write in internal forums of the community.

Interaction between users and aesthetic companies (FIG. 12, 170):
a. users may contact companies and become followers,
b. users may order products from the companies online,
c. users may use the services provided by these companies in the community,
d. users may comment and rate these companies,
e. companies may launch marketing campaigns and special offers to users,
f. companies may provide 3D simulation services of their own products, and/or
g. companies may test new products before they are launched in the market to gain market studies.

Interaction between users and aesthetic professionals (FIG. 12, 180):
a. users may contact aesthetic professionals and become followers,
b. users may send their 3D results to professionals and ask for advice,
c. users may send their 3D results to professionals and ask for a consultation,
d. users may plan the procedure, book a date and/or calculate prices per procedure,
e. users may comment and/or rate these professionals,
f. users may recommend aesthetic professionals to other users,
g. professionals may launch marketing campaigns and/or special offers to users, and/or
h. professionals may provide 3D simulation services and/or remote consultation.

Interaction between aesthetic professionals and aesthetic companies (FIG. 12, 190):
a. aesthetic professionals may contact companies and become followers,
b. aesthetic professionals may order products online from companies,
c. companies may launch marketing campaigns and/or offers to professionals, and/or
d. companies may provide 3D simulation services of their own products.

Consumers being part of the community may be able to contact the aesthetic professionals through a finder tool (FIG. 12, 130), with different search options like distance from consumer's address, location, ratings, procedures done, endorsements, 3D availability, comparisons between real outcomes and/or 3D simulations.

Aesthetic professionals may have a search ranking based on the above parameters, but different options may be provided in order to let them move up in the ranking based for example on a paying service. Such paying service may let them appear in preferential sections of the application, for example when a consumer is simulating a specific 3D procedure or 3D simulation feature. For example, a plastic surgeon may pay to appear in the page of consumers in a certain city whenever they are doing a simulation of breast augmentation. A promotional banner may appear in a specific part of the page. Different parts of the page may be defined for higher or lower priorities and/or prices.

Consumers may also contact the aesthetic companies being members of the community. Such companies may have a profile sharing all the information desired to the community about their products and/or services. There may be aesthetic companies targeting consumers, such as cosmetics manufacturers, and other targeting aesthetic professionals such as sutures manufacturers, and others targeting both, such as Botox® or breast implants manufacturers.

The platform may include a search tool (FIG. 12, 120) with different search options like type of product, type of procedure, ratings, recommendations and/or 3D simulators available.

Aesthetic professionals and companies inside the community may have access to their respective search tools, for example breast implant manufacturers looking for plastic surgeons and/or dermatologists looking for dermal filler producers.

All interaction between users, aesthetic professionals and companies (FIG. 12, 160, 170, 180, 190) may be done directly between them or through the Core 3D simulation features (FIG. 12, 110) available in the community.

Accordingly, in a third aspect, the present teaching provides a community or 3D virtual world of users and/or entities (FIGS. 12, 100, 140 and 150), wherein said community or 3D virtual world is an online platform characterized in that:

at least one user and/or entity of said community or 3D virtual world use at least one method according to any of the previous claims, said users and/or entities may possess at least one 3D representation and/or 3D simulation and with the possibility to interact with other users (FIG. 12, 10+20; FIG. 12, 110), said entities comprise aesthetic professionals, aesthetic or beauty companies, and/or institutions, with the possibility to generate at least one 3D representation of their bodies, intangible or tangible assets, trademarks, products or services, with the possibility to generate at least one 3D simulation, and with the possibility to interact with the community (FIGS. 12, 100, 140 and 150; FIG. 12, 10+20; FIG. 12, 110), said community comprise different types of accounts or members: consumers, aesthetic professionals, aesthetic companies, associations and/or groups (FIGS. 12, 100, 140 and 150), said users and entities possessing at least one 3D representation and/or 3D simulation become a 3D user of the community (FIG. 12, 100), said users and entities may simulate using the different available simulation options (FIG. 12, 110), interact with other users inside the community (FIG. 12, 160; FIG. 12, 170; FIG. 12, 180), use a search tool to find an aesthetic professional (FIG. 12, 130), use a search tool to find an aesthetic company providing services in the community (FIG. 12, 120), interact with aesthetic professionals and aesthetic companies (FIG. 12, 170; FIG. 12, 180), and/or share the experience inside the community with other contacts through other social networks and/or communities (FIG. 12, 200), said users, consumers and/or entities may select the level of privacy, said aesthetic professionals and/or aesthetic companies may propose their services to all the users, be listed in the finder tool (FIG. 12, 110; FIG. 12, 120), be found by users, aesthetic companies and/or aesthetic professionals, and/or actively participate in the activities inside the community, said members may interact with each other (FIG. 12, 190), in a one to one interaction, a one to several interaction and/or several to several interaction, said interaction being either private, partially private or public, said interaction being made either directly between said members or through the Core 3D simulation features available in the community (FIG. 12, 110), said user to user interaction and/or action consists of or comprise (FIG. 12, 160):
a. make friendship requests,
b. share 3D results with other users or groups of users,
c. make comment in own 3D results or others' results,
d. participate in public, partially private and/or private conversations,
e. put ratings in own 3D results or others' results,
f. vote for best 3D results,
g. propose 3D visualizations of friends with the option to select or vote for the most attractive 3D visualization,
h. create videos with own 3D results and optionally share them with others,
i. participate in competitions between users, and/or
j. write in internal forums of said community.

Said user to aesthetic company interaction and/or action consists of or comprise (FIG. 12, 170):
a. contact companies and become followers,
b. order products from the companies online,
c. use the services provided by the companies in the community, and/or
d. comment and rate these companies.

Said aesthetic company to user interaction and/or action consists of or comprise (FIG. 12, 170):
a. launch marketing campaigns and special offers to users,
b. provide 3D simulation services of their own products, and/or
c. test new products before they are launched in the market to gain market studies.

Said users to aesthetic professionals interaction and/or action consists of or comprise (FIG. 12, 180):
a. contact aesthetic professionals and become followers,
b. send their 3D results to professionals and ask for advice,
c. send their 3D results to professionals and ask for a consultation,
d. plan the procedure, book a date and calculate prices per procedure,
e. comment and rate these professionals, and/or
f. recommend aesthetic professionals to other users.

Aesthetic professionals to users interaction and/or action consists of or comprise (FIG. 12, 180):
a. launch marketing campaigns and special offers to users, and/or
b. provide 3D simulation services and remote consultation.

Said aesthetic professionals to aesthetic companies interaction and/or action consists of or comprise (FIG. 12, 190):
a. contact companies and become followers, and/or
b. order products online from companies.

Said aesthetic companies to aesthetic professionals interaction and/or action consists of or comprise (FIG. 12, 190):
a. launch marketing campaigns and/or offers to professionals, and/or
b. provide 3D simulation services of their own products.

Said member(s) of the community may contact other member(s) through a finder tool (FIG. 12, 120, 130), said finder tool having different search options available selected from distance from consumer's address, location, ratings, procedures done, endorsements, 3D availability, and/or comparisons between real outcomes and 3D simulations, said member(s) of the community may have a search ranking based on the parameters of said finder tool, with different options provided in order to let said member(s) move up in the ranking based on a paying service, said member(s) of the community may use a paying service in order to let said member appear in preferential sections of the application or of the method according to any of the previous claims, said aesthetic companies may possess a profile in order to share all the information desired to the community about their products and services, wherein said aesthetic companies have the option to target either consumers only, aesthetic professionals only or consumers and aesthetic professionals, said member(s) of the community may use a search tool having different search options selected from type of product, type of procedure, type of member, ratings, recommendations, profile, and/or available 3D simulators, wherein said search tool is adapted to the type of member, and/or said member(s) of the community, the owner of said platform, the developer or owner of said community, the system owner, a software or program developer, and/or a software company may develop applications to be integrated in said platform or community.

Accordingly, in a sixteen preferred embodiment, the present teaching provides a method according to the third aspect of the present teaching, wherein said members may create 3D virtual shops and sell their creations to other members, and/or wherein said creations are selected from 3D models of clothes, accessories, or creations based on other member's 3D representations.

The core 3D simulation features or 3D procedure may also be selected from:

3D creation, wherein the consumer may create its 3D representation by using photos or video. The 3D representations are stored in his account, and they may be visible by others if allowed by the user according to privacy settings, breast surgery simulation wherein the simulation is selected from breast augmentation, breast reduction, breast lift breast reconstruction, breast implant revision and/or any other breast-related procedure, facial surgery simulation wherein the simulation is selected from different surgeries such as rhinoplasty, face lifting, eyelid surgery, cheek implants, chin implants, fat injection, brow lift, ears surgery and/or hair transplantation, facial aesthetic procedures wherein the simulation is selected from Botox®, dermal fillers, threads, hyaluronic acid, PRP and/or any other facial procedure, body procedures, wherein said body procedure is selected from tummy tuck, abdominoplasty, body sculpturing, liposuction, and/or any other body procedure, movement sequences, wherein the movement sequence is selected from 3D animations of different parts of the body with different movements selected from running, jumping, and/or any other body movement, video creation, wherein the video creation uses a tool to create video sequences from the 3D content generated. Such videos may be shared with other users, members and/or in other social networks, facial gestures simulation, wherein the simulation consists of 3D animations of different facial expressions selected from laughing, crying, smiling, and/or any kind of simulations that can provide a living-look to the 3D representation, cosmetics and make-up, wherein the simulation is selected from make-up and/or effects of different types of cosmetics. The types and parameters for each product simulated might be provided by aesthetic companies or by the system. An ordering system tool may be provided for each product, virtual clothes, wherein the simulation consists of 3D clothes. It may be composed of different collections provided by aesthetic and/or fashion companies, created by the system, and/or by letting the users create their own 3D clothes. They may be full body clothes or partial. An ordering system tool may be provided for each product, glasses and facial accessories, wherein the simulation is selected from glasses, facial accessories such as piercings, earrings, and/or any other accessory. The products may be provided by the manufacturers, by the system, and/or letting the users create their own 3D accessories. An ordering system tool may be provided for each product, younger/older tools, wherein the simulation consists of changes to the morphology of the face and/or body depending on the age, thin/fat tools, wherein the simulation consists of change to the morphology of the face and/or body depending on the weight/bmi, morphing to celebrity tool, wherein the 3D morphing tool consist of mixing the face of the user and a specific celebrity, find your celebrity match, wherein said tool consists of searching for the closest celebrity matching your or a selected facial 3D morphology, morphing to friend tool, wherein said 3D morphing tool consist of mixing or combining the face of the user with another user, find your 3D match, wherein said tool consists of searching for a user in the community, 3D virtual world, or online matching the morphological parameters specified by the user, matching the 3D representation and/or 3D simulation, 3D daily horoscope, wherein the feature provides the user with the horoscope, and it applies the state of mood and emotions into the 3D facial model of the user. Such 3D facial model is available as the avatar of the user on his profile, and may be public to friends and/or other users. Friends may share or follow their 3D horoscopes. The possibility to apply the state of mood and emotions into the 3D facial model or 3D anatomical output of the user may also be independent of the horoscope. For example, the user might select among different moods and emotional states and the system will simulate generating a 3D simulation, rental/license/sale of 3D images, wherein anyone may rent, license and/or sell the different parts of the body or full body generated by the system. Those may be used for communication, movie, games, sex, and any other purpose, dating, wherein the feature may use aesthetic matching solutions for finding people that fit best selected morphologic criteria and/or wherein the feature may use the creation of an avatar to search for similar and/or close ones.

In a seventeen preferred embodiment, the present teaching provides a method according to any of the aspects or embodiments of the present teaching, wherein said 3D procedure or 3D simulation feature is selected from breast procedure, facial procedure, gluteus procedure, muscle procedure, rhinoplasty procedure, cranio-maxillo-facial procedure, breast surgery simulation, facial surgery simulation, facial aesthetic procedure or any other procedure in the plastic, reconstructive or aesthetic field, 3D creation, body procedure, movement sequence, video creation, facial gestures simulation, cosmetics and make-up simulation, virtual clothes, glasses and facial accessories, younger/older tools, thin/fat tools, morphing to celebrity tool, find your celebrity match, morphing to friend tool, find your 3D match, 3D daily horoscope, rental, license and/or sale of 3D images, and/or dating.

In another aspect, the present teaching provides a 3D virtual world, with all the characteristics of a 3D virtual world like 3D buildings, 3D roads, 3D objects, i.e. all things represented in 3D, wherein at least one 3D representation of an animal or human is obtained by any method according to the present teaching. Such virtual world may contain any creation, object, accessory, or product obtained according to any method of the present teaching, according to the second aspect of the present teaching and/or wherein any core 3D simulation feature and/or 3D procedure may be performed. Any or all characteristics or features herein described for the community or else may similarly apply to the 3D virtual world.

In a fourth aspect, the present teaching provides a use of any method of the present teaching, a product, object, accessory, medical device, implant, sizer or any creation according to the second aspect of the present teaching, a community or 3D virtual world or platform according to the third aspect of the present teaching for/enabling:

aesthetic professional to show consumers or any users or members to show to any other user(s) or member(s) selected 3D anatomical outcome(s) based on selected features and/or desired outcome, and/or selected product, object, medical device, implant, or sizer obtained by any method of the present teaching, consumers to send photo(s) through an online access or mobile application, requesting a specific aesthetic procedure, wherein the consumer gets the 3D results through the aesthetic professional, either during the consultation or by remote consultation, consumers to send their photos through an online access or mobile application, and after paying the service fee, the consumer gets the 3D results online, aesthetic professionals to use the 3D system to simulate the desires of the consumer, and to request and/or produce themselves a product, object, creation and/or accessory to be used by the consumer, aesthetic professionals to use the 3D system to simulate the desires of the consumer, and to request or produce themselves a custom sizer to be used by the consumer, aesthetic professionals to use the 3D system to simulate the desires of the consumer, and to request or produce themselves a custom implant to be used during the surgery, consumers to create an account in the system's community, platform or virtual world, create their 3D representations and share them with other members, wherein during the process of simulating at least one aesthetic procedure said member may contact at least one aesthetic professional in order to get a consultation, may order online specific beauty products, and/or play with the different 3D tools or games available in said community, and/or aesthetic professionals to create an account in the system's community, platform or virtual world and pay for premium options such as top ranking in the search section of professionals, to launch promotions to all members, and/or to contact aesthetic companies to order products.

A 3D procedure or 3D simulation herein described may be applied to any aspect or any embodiment of the present teaching. A 3D procedure or 3D simulation may for example apply to any step of generating a 3D (anatomical) output.

In one embodiment, a method according to any aspect or embodiment of the present teaching allows the synthesis, fabrication, creation and/or manufacturing of an object, product, medical device, implant, sizer, accessory, body or face accessory, cloth, Botox®, dermal filler, sutures, plates or any other product or object that may be integrated in a 3D simulation procedure.

In one embodiment, a method, 3D procedure or 3D simulation feature according to any aspect or embodiment of the present teaching may be applied on internal organs, tissue, bone and/or cartilage.

In one embodiment, a method, 3D procedure or 3D simulation feature according to any aspect or embodiment of the present teaching is performed automatically. For example, 3D simulation procedures may be performed automatically.

In one embodiment, a method, step, 3D procedure or 3D simulation feature according to any aspect or embodiment of the present teaching may be performed either solely by a user, a virtual assistant or a professional. Alternatively, any step performed by a user may be performed by a relative, virtual assistant or professional. Alternatively, it may be performed in a collaborative manner.

Preferably, a method according to any aspect or embodiment of the present teaching is applied on humans.

Preferably, a 3D procedure or 3D simulation feature according to any aspect or embodiment of the present teaching is an aesthetic or plastic procedure.

All the aspects and embodiments of the present teaching also apply for example to facial 3D simulations, wherein the user may order product(s) related to facial aesthetics in the same way as described for breasts. When ordering a product, the order(s) may also be sent from other parts of the online platform, not only in the 3D visualization step or location. In one embodiment, ordering may be done from the online platform. In another embodiment, ordering may be done from the online platform, from the patient profile directly and/or in a more general way from the homepage.

EXAMPLES

Example 1

A prototype is being developed related to a method of the present teaching, wherein a consumer can access an online service provided by the system and where he can get a 3D simulation of a desired procedure. Once the consumer clicks on such service, a video appears explaining what the results could be and how to take the photos (as guidelines or help function). Then, the consumer enters into a step where three photos must be uploaded to the system, together with some physical and personal information. After that, the consumer must enter his credit card details for the payment of this service, and finally he ends up in a dashboard page where he is informed about the process being held. Once the 3D representation and simulation is done, the consumer gets an access to visualize the 3D representation and simulation through the dashboard.

Figure 15:
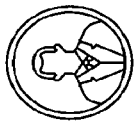
FIG. 15 is a screenshot representing the step of adding the contact information after uploading the photos.
Figure 16:
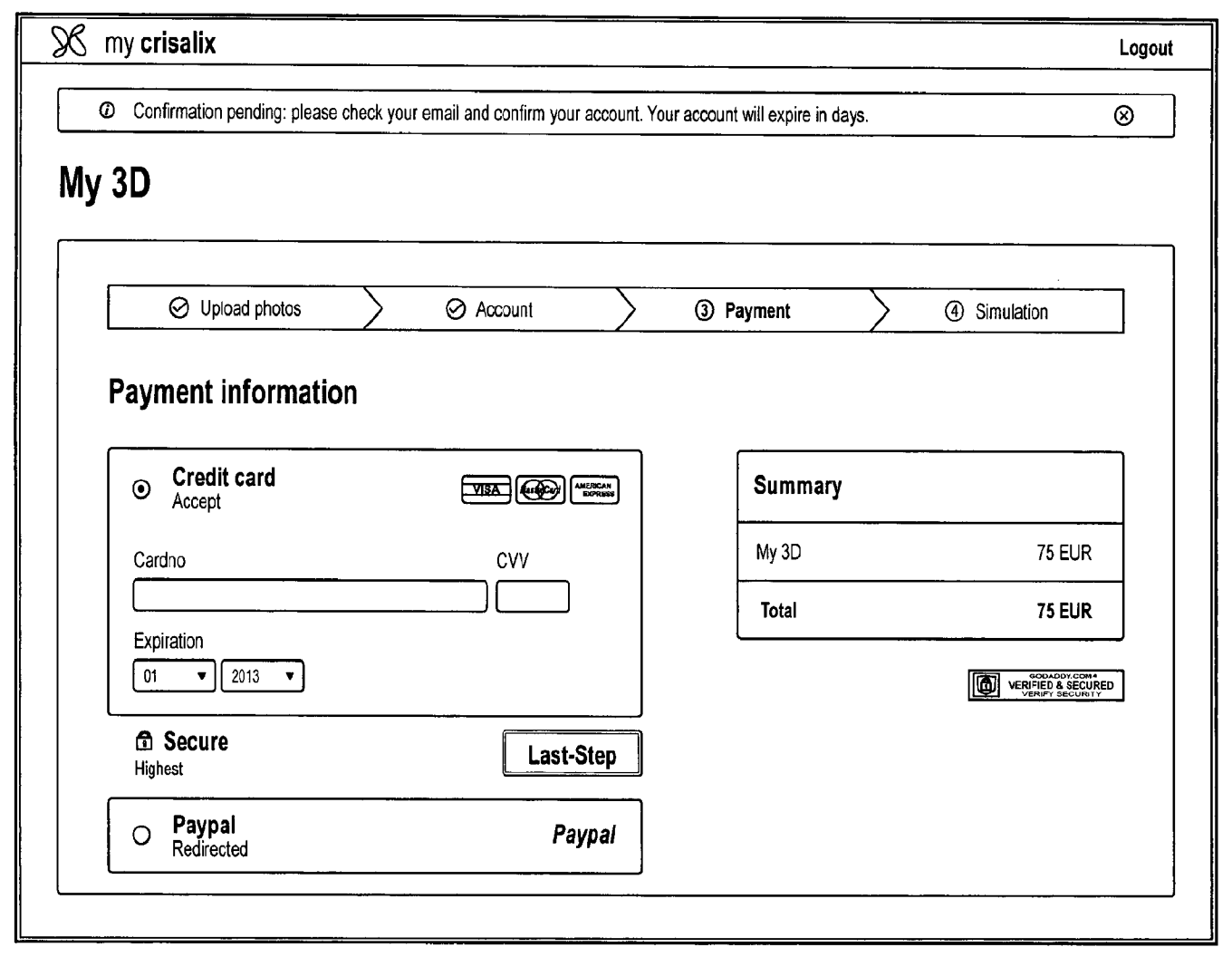
Figure 17:
FIG. 17 is a screenshot representing the communication feed to show the status of the 3D generation.

A few screenshots representing some steps of the method have been taken. FIG. 14 is a screenshot representing the step dedicated to upload the 3 photos needed to create the 3D representation (see also FIG. 2). FIG. 15 is a screenshot representing the step of adding the contact information after uploading the photos (see also FIG. 2, 10.4). FIG. 16 is a screenshot representing the step of adding the credit card information to proceed to payment for the 3D service. FIG. 17 is a screenshot representing the communication feed to show the status of the 3D generation.

Example 2

Example 2 represent prototypes of a few aspects/embodiments of the present teaching illustrated by screenshots of the application (including first aspect, 14.sup.th and 15.sup.th embodiments of the present teaching).

Figure 18:
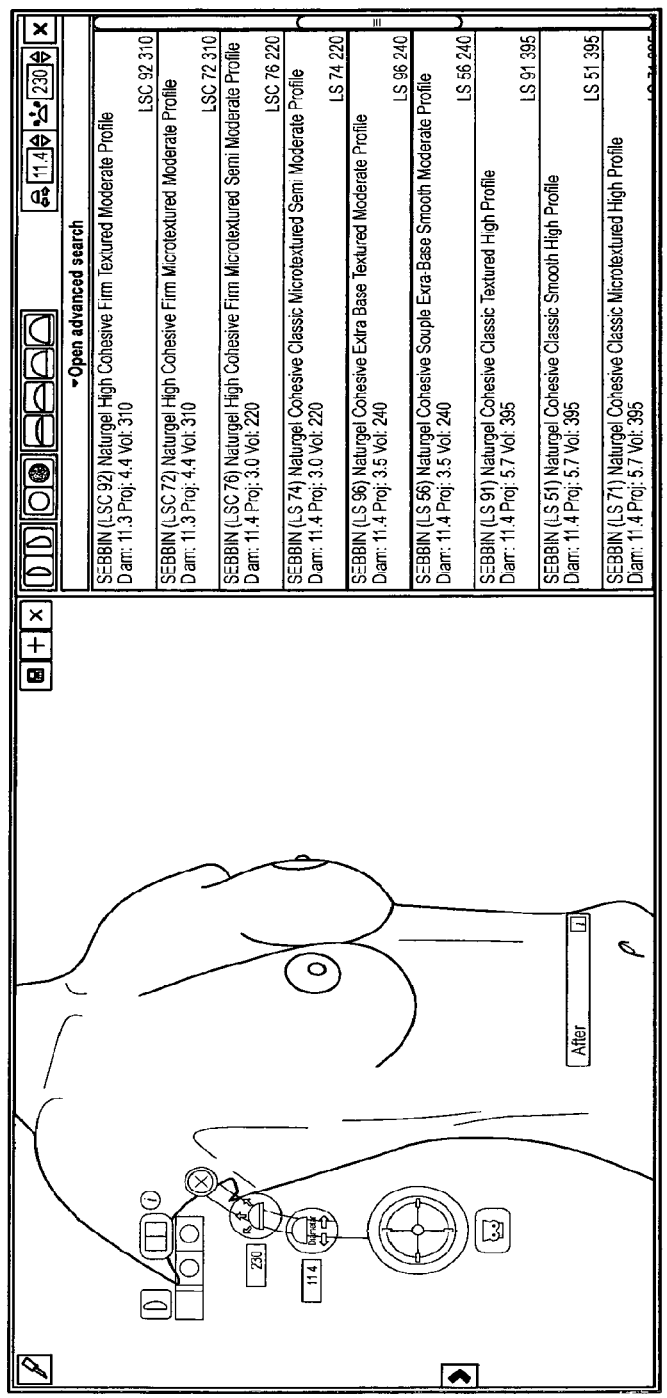
FIG. 18 is a screenshot representing the 3D viewer showing the simulation of a patient with a specific volume, with the catalog of implants on the right side and the "knife" button on the top-left corner.

After the 3D simulation procedure, with the selection of the desired implants by the patient, results are directly displayed to the user (e.g. patient or doctor), see FIG. 18. Hence, the user may select currently manufactured implants that are integrated in the system (database) and immediately see the results on his computer and/or any other displaying device (multiple displaying devices may be used for displaying the results).

Figure 19:
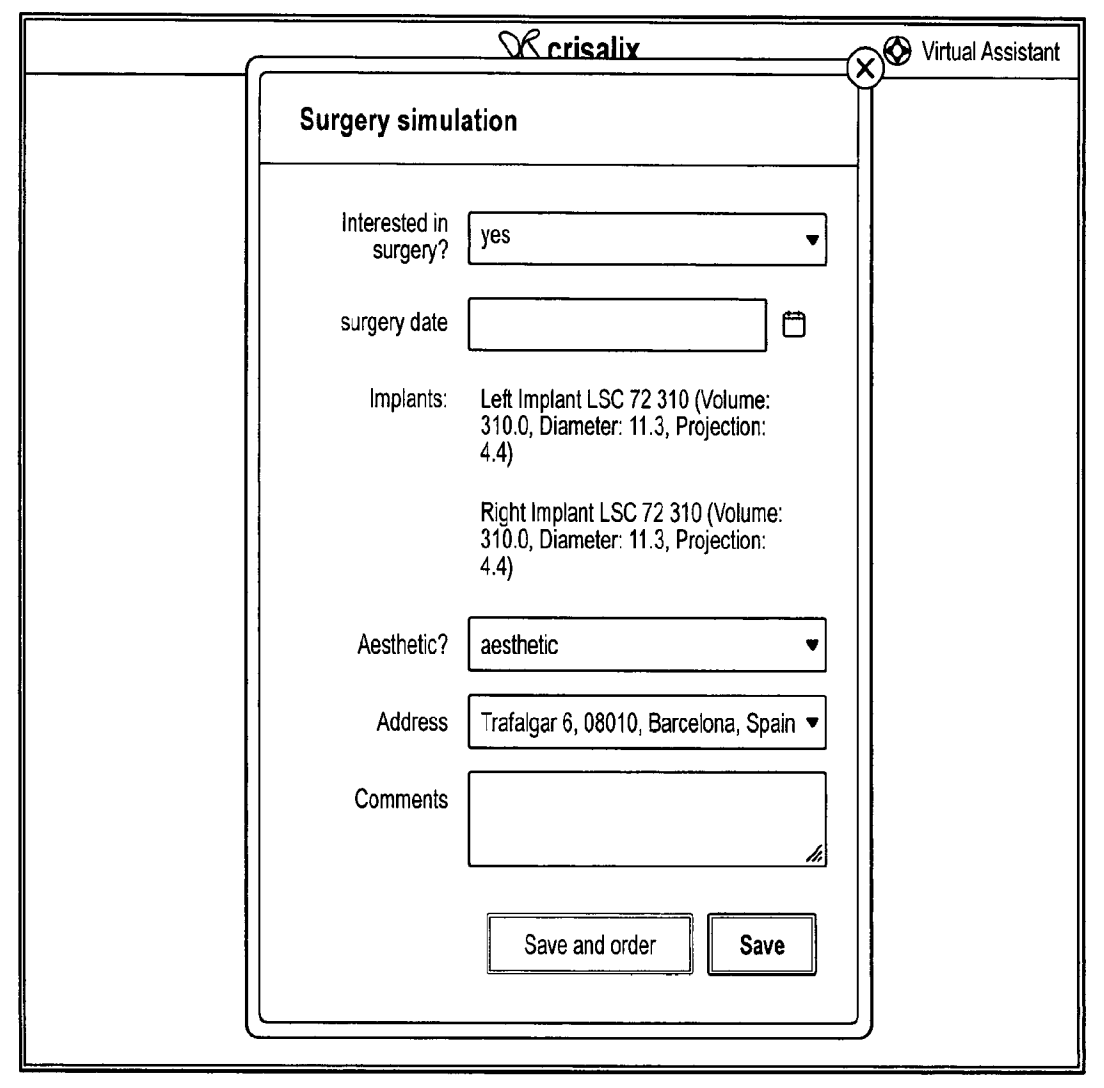

Once the user (e.g. patient and/or doctor) has made his choice among the different available 3D results by selecting one 3D result, he just have to click on the button "knife" on the top-left corner to open the ordering form (see FIG. 19). The ordering form indicates the specific type of implants simulated with the following information for each implant (left and right implants): type of implant, volume required, diameter and projection. On this form, the user (e.g. patient or doctor) may specify the date of surgery, the type of surgery between aesthetic or reconstructive, the address of delivery of the implants and write some comments. By clicking on the button "Save and order", the user launches the ordering system.

Once the order has been made, mobile messages and emails are sent to the set of contacts the doctor has defined on his account. A Customer Relationship Manager (CRM) system is available wherein for any surgeon a list of contacts may be entered, defining who receives notifications only and/or who is the responsible of confirming the order (herein may be designated as the "master"). All notifications may be set to SMS, email or both and/or any other communication tool/channel.

Both the doctor and the distributor/merchant/manufacturer have a list of orders with the current status (pending, confirmed, cancelled), with all details about each order (including creation date, comments, patient information and implants ordered). Other options like stock management, products availability and tracking system are being added.

Accordingly, the present teaching provides a method of generating at least one 3D anatomical output, 3D representation and/or 3D simulation of an animal body or human body and/or of at least one part of said body and thereafter selecting, ordering, creating/producing and/or delivering/receiving at least one product derived from said 3D output/representation/simulation consisting of or comprising:
  i) optionally accessing service (FIG. 7, 60),
  ii) optionally starting process (FIG. 7, 70),
  iii) optionally linking users together, wherein said users are selected from consumers, professionals (e.g. healthcare professionals) and companies (e.g. manufacturers) (FIG. 7, 80),
  iv) receiving as input at least one image, at least one video and/or anatomical information (FIG. 1, 10)
  v) generating at least one 3D anatomical output from said body and/or of at least one part of said body (FIG. 1, 20),
  vi) optionally visualizing said 3D anatomical output (FIG. 1, 30),
  vii) optionally linking users together, wherein said users are selected from consumers, professionals and companies (FIG. 7, 80),
  viii) optionally selecting at least one 3D anatomical output,
  ix) optionally online ordering of at least one product (FIG. 6, 50), with the option of selecting a professional providing advice and/or performing any kind of assistance, activity and/or procedure related to said ordered product, x) optionally informing persons and/or users of said ordering, xi) optionally generating a list of orders made and/or received for each user, xii) optionally creating/producing at least one object, creation, product, accessory, implant and/or sizer from said 3D anatomical output (FIG. 5, 40), xiii) optionally delivering/receiving at least one object, creation, product, accessory, implant and/or sizer, xiv) optionally managing stock, xv) optionally determining product(s) availability, xvi) optionally using a tracking system, xvii) optionally data mining, and xviii) optionally producing statistics.

The skilled artisan will understand that the order of the steps of any aspects of the present teaching may be easily modified and the present teaching shall not be limited to the specific order disclosed herein. For example, the step of linking users together may be made anytime during the process.

A user may be a customer, patient, doctor, healthcare professional, healthcare center/institution, hospital, private practice, manufacturer or distributor.

Selection of at least one 3D anatomical output according to step viii) may be made by simple clicking on a button (e.g. "knife" button).

Ordering of at least one product according to step ix) may be made via an ordering form, which may comprise the following information for each product selected (e.g. left and right implants): type of product (e.g. implant), shape, size or volume required, specific measures (e.g. diameter for implant), color (or black and white, gray scale) and/or projection. On this form, the customer (e.g. patient) may select a professional (e.g. doctor) that will provide advice and/or perform any kind of assistance, activity and/or procedure (e.g. surgical procedure) related to the product selected or ordered. On this form, the user (e.g. patient or doctor) may also specify:

i) the date (optionally multiple dates selected with definitive choice made later, optionally in agreement with other users, doctors and/or else) and eventually time of any assistance, activity and/or procedure linked to the product ordered (e.g. surgery) and/or to the delivery of the product, ii) the type of assistance, activity and/or procedure (e.g. surgery, between aesthetic or reconstructive), iii) the address of delivery of the product (e.g. implants), and/or iv) write some comments.

Ordering of the product(s) may be made by simple clicking on a button (e.g. "Save and order" button).

All the aspects and embodiments of the present teaching also apply for example to facial 3D simulations, wherein the user may order product(s) related to facial aesthetics in the same way as described for breasts. When ordering a product, the order(s) may also be sent from other parts of the online platform, not only in the 3D visualization step or location. In one embodiment, ordering may be done from the online platform. In another embodiment, ordering may be done from the online platform, the patient profile directly and/or in a more general way from the homepage.

The step of informing persons and/or users of the ordering according to step x) may be made via mobile messages and/or emails, which may be sent to the set of contacts the doctor and/or user has defined on his account. The step of informing persons and/or users of the ordering according to step x) may take the form of a Customer Relationship Manager (CRM) system wherein for any user (e.g. surgeon) a list of contacts may be entered, defining who receives notifications only and/or who is the responsible of confirming the order. All notifications may be set to SMS, email or both and/or any other communication tool/channel.

The step of generating a list of orders made and/or received for each user according to step xi) may take the form of a list of orders with the current status (for example pending, confirmed or cancelled), and may comprise all details about each order, including creation date, comments, user information and/or product ordered (e.g. implants). Such lists of orders may be generated for the doctor and the distributor/merchant/manufacturer. For example, in the case of a patient, all products that a patient has ordered are displayed at least to him (information may be shared to another user or other person). For example, in the case of a doctor, all products that have been ordered by any patient selecting this doctor are displayed to at least this doctor (information may be shared to another user or other person). For example, in the case of a manufacturer, all orders made by any user ordering a product manufactured by this manufacturer are displayed to at least the manufacturer (information may be shared to another user or other person).

Other options like stock management, products availability and tracking system are being added.

Advantageously, such aspects/embodiments of the present teaching increase the conversion rate of plastic surgeons through 3D simulation and enables online ordering of medical products with just one click.

With the present ordering platform, users (doctors and patients) may simulate the aesthetic procedure, agree on the desired outcome (e.g. doctors agree with the patients), and order the corresponding medical products needed all in the same process.

Here are just a few of the advantages such system brings to medical merchants/manufacturers:

save considerable time, workflow and costs related to the ordering process, increase turnover and commissions per sales representative by keeping them dedicated on client relationship and acquisition, increase sales through direct and easy order access, competitive edge towards other medical merchants, diminish inventories and errors, and offer and manage all merchants/manufacturers' products portfolio through the same platform.

What is claimed is:

1. A system with machine readable media executing on a processor for simulating an aesthetic procedure to be performed on a body part, comprising: a modelling application for receiving an input comprising an image of the body part and an anatomical measurement of the body part, and for generating a 3D representation of the body part based on the input; a 3D editor enabling a user to modify the 3D representation to correct inaccuracies in the 3D representation; a catalog of a plurality of products or services each associated with an aesthetic procedure; a planning interface for displaying the 3D representation to a user and enabling the user to plan an aesthetic procedure by selecting one of the plurality of products or services in the catalog; a simulation application for generating a 3D simulation of an outcome of the aesthetic procedure based on the selected product or service and the 3D representation; a viewer for displaying the 3D simulation so the user can virtually pre-visualize the impact on the body part of performing the aesthetic procedure associated with the selected one of the plurality of products or services.

2. The system of claim 1, wherein the 3D editor further enabling a user to modify the 3D representation to define a desired outcome; the system further comprising a backwards simulation application for receiving the desired outcome, for calculating the changes to the body part to obtain the desired outcome, and for determining a product or service to reach the desired outcome.

3. The system of claim 1, wherein the aesthetic procedure is a breast implant procedure, the system further comprising a 3D printer for creating a non-implantable, wearable breast implant sizer for physically pre-visualizing the outcome of performing the breast implant procedure.

4. The system of claim 1, wherein the input to the modelling application comprises a video of the body part, the modelling application extracting a frame from the video to obtain the image of the body part.

5. The system of claim 1, further comprising a search tool to select an aesthetic professional for performing the aesthetic procedure associated with the selected product or service, at least one of the 3D representation and the 3D simulation sent electronically to the selected aesthetic professional with a request for a consultation regarding the aesthetic procedure.

6. The system of claim 1, wherein the selected one of the plurality of products or services comprises an implant, and the planning interface enables the user to change a size and position of the implant.

7. The system of claim 1, wherein the selected one of the plurality of products or services comprises an injection, and the planning interface enables the user to change a volume of the injection.

8. The system of claim 1, further comprising a mobile device having a camera for taking the image and providing the image to the modelling application over a network.

9. The system of claim 1, wherein the viewer compares the initial 3D representation with the 3D simulation in an animation that progressively shows a change.

10. The system of claim 1, wherein the 3D simulation comprises simulating different facial expressions.

11. The system of claim 1, further comprising an online, virtual community connecting the user with other users.

12. The system of claim 11, wherein the virtual community enables the user to share the 3D simulation with said other users in the community and to receive feedback.

13. The system of claim 12, wherein the feedback comprises an alternative 3D simulation generated by one of said other users.

14. The system of claim 11, wherein the virtual community enables a user comprising a product manufacturer to offer 3D simulations of a new product before launching the product to perform a market study.

15. A computing-machine implemented method executing on a processor for simulating an aesthetic procedure to be performed on a body part, comprising: receiving an input comprising an image of the body part and an anatomical measurement of the body part, and generating a 3D representation of the body part based on the input; enabling a user to modify the 3D representation to correct inaccuracies in the 3D representation; providing a catalog of a plurality of products or services each associated with an aesthetic procedure; displaying the 3D representation to a user and enabling the user to plan an aesthetic procedure by selecting one of the plurality of products or services in the catalog; generating a 3D simulation of an outcome of the aesthetic procedure based on the selected product or service and the 3D representation; displaying the 3D simulation so the user can virtually pre-visualize the impact on the body part of performing the aesthetic procedure associated with the selected one of the plurality of products or services.

16. The method of claim 15, further comprising:
enabling the user to modify the 3D representation to define a desired outcome;
using a backwards simulation application to calculate the changes to the body part to obtain the desired outcome and to determine a product or service to reach the desired outcome.

17. The method of claim 15, wherein the aesthetic procedure is a breast implant procedure, and the method further comprises controlling a 3D printer to create a non-implantable, wearable breast implant sizer for physically pre-visualizing the outcome of performing the breast implant procedure.

18. The method of claim 15, wherein the step of receiving an input comprises receiving a video of the body part and extracting a frame from the video to obtain the image of the body part.

19. The method of claim 15, further comprising:
selecting, via a search tool, an aesthetic professional for performing the aesthetic procedure associated with the selected product or service; and
transmitting at least one of the 3D representation and the 3D simulation to the selected aesthetic professional with a request for a consultation regarding the aesthetic procedure.

20. The method of claim 15, further comprising:
providing an animation which progressively shows a change between the initial 3D representation and the 3D simulation.

* * * * *